United States Patent
Thompson-Nauman et al.

(10) Patent No.: US 11,857,779 B2
(45) Date of Patent: Jan. 2, 2024

(54) IMPLANTABLE CARDIOVERTER-DEFIBRILLATOR (ICD) SYSTEM INCLUDING SUBSTERNAL PACING LEAD

(71) Applicant: Medtronic, Inc., Minneapolis, MN (US)

(72) Inventors: Amy E. Thompson-Nauman, Ham Lake, MN (US); Melissa G. T. Christie, Andover, MN (US); Paul J. DeGroot, Shoreview, MN (US); Rick D. McVenes, Isanti, MN (US); Becky L Dolan, Chisago, MN (US)

(73) Assignee: Medtronic, Inc., Minneapolis, MN (US)

( * ) Notice: Subject to any disclaimer, the term of this patent is extended or adjusted under 35 U.S.C. 154(b) by 69 days.

(21) Appl. No.: 16/742,385

(22) Filed: Jan. 14, 2020

(65) Prior Publication Data
US 2020/0147402 A1 May 14, 2020

Related U.S. Application Data

(62) Division of application No. 14/261,456, filed on Apr. 25, 2014, now Pat. No. 10,556,117.
(Continued)

(51) Int. Cl.
*A61N 1/05* (2006.01)
*A61N 1/39* (2006.01)

(52) U.S. Cl.
CPC ........... *A61N 1/05* (2013.01); *A61N 1/39622* (2017.08)

(58) Field of Classification Search
CPC .............................. A61N 1/05; A61N 1/39622
See application file for complete search history.

(56) References Cited

U.S. PATENT DOCUMENTS

| | | |
|---|---|---|
| 3,614,954 A | 10/1971 | Mirowski et al. |
| 3,706,313 A | 12/1972 | Milani et al. |

(Continued)

FOREIGN PATENT DOCUMENTS

| | | |
|---|---|---|
| CN | 1859870 A | 11/2006 |
| CN | 102858403 A | 1/2013 |

(Continued)

OTHER PUBLICATIONS

Preliminary Amendment from U.S. Appl. No. 16/725,458, dated Mar. 25, 2020, 7 pp.
(Continued)

*Primary Examiner* — Mark W. Bockelman
(74) *Attorney, Agent, or Firm* — Shumaker & Sieffert, P.A.

(57) ABSTRACT

An implantable cardiac defibrillator (ICD) system includes an ICD implanted subcutaneously in a patient, a defibrillation lead having a proximal portion coupled to the ICD and a distal portion having a defibrillation electrode configured to deliver a defibrillation or cardioversion shock to a heart of the patient, and a pacing lead that includes a distal portion having one or more electrodes and a proximal portion coupled to the ICD. The distal portion of the pacing lead is implanted at least partially along a posterior side of a sternum of the patient within the anterior mediastinum. The ICD is configured to provide pacing pulses to the heart of the patient via the pacing lead and provide defibrillation shocks to the patient via the defibrillation lead. As such, the implantable cardiac system provides pacing from the substernal space for an extravascular ICD system.

21 Claims, 11 Drawing Sheets

Related U.S. Application Data

(60) Provisional application No. 61/819,866, filed on May 6, 2013, provisional application No. 61/819,984, filed on May 6, 2013.

(56) References Cited

U.S. PATENT DOCUMENTS

| | | |
|---|---|---|
| 4,030,509 A | 6/1977 | Heilman et al. |
| 4,146,037 A | 3/1979 | Flynn et al. |
| 4,270,549 A | 6/1981 | Heilman |
| 4,280,510 A | 7/1981 | O'Neill |
| 4,291,707 A | 9/1981 | Heilman et al. |
| 4,437,475 A | 3/1984 | White |
| 4,450,527 A | 5/1984 | Sramek |
| 4,512,351 A | 4/1985 | Pohndorf |
| 4,538,624 A | 9/1985 | Tarjan |
| 4,693,253 A | 9/1987 | Adams |
| 4,708,145 A | 11/1987 | Tacker, Jr. et al. |
| 4,765,341 A | 8/1988 | Mower et al. |
| 4,787,389 A | 11/1988 | Tarjan |
| 4,832,687 A | 5/1989 | Smith, III |
| 4,865,037 A | 9/1989 | Chin et al. |
| 4,953,551 A | 9/1990 | Mehra et al. |
| 5,036,854 A | 8/1991 | Schollmeyer et al. |
| 5,099,838 A | 3/1992 | Bardy |
| 5,105,810 A | 4/1992 | Collins et al. |
| 5,113,869 A | 5/1992 | Nappholz et al. |
| 5,125,904 A | 6/1992 | Lee |
| 5,129,392 A | 7/1992 | Bardy et al. |
| 5,176,135 A | 1/1993 | Fain et al. |
| 5,193,539 A | 3/1993 | Schulman et al. |
| 5,193,540 A | 3/1993 | Schulman et al. |
| 5,203,348 A | 4/1993 | Dahl et al. |
| 5,255,691 A | 10/1993 | Otten |
| 5,255,692 A | 10/1993 | Neubauer et al. |
| 5,261,400 A | 11/1993 | Bardy |
| 5,273,053 A | 12/1993 | Pohndorf |
| 5,292,338 A | 3/1994 | Bardy |
| 5,300,106 A | 4/1994 | Dahl et al. |
| 5,312,355 A | 5/1994 | Lee |
| 5,331,966 A | 7/1994 | Bennett et al. |
| 5,336,252 A | 8/1994 | Cohen |
| 5,342,407 A | 8/1994 | Dahl et al. |
| 5,366,496 A | 11/1994 | Dahl et al. |
| 5,376,105 A | 12/1994 | Hedberg |
| 5,385,574 A | 1/1995 | Hauser et al. |
| 5,411,539 A | 5/1995 | Neisz |
| 5,423,326 A | 6/1995 | Wang et al. |
| 5,439,484 A | 8/1995 | Mehra |
| 5,441,504 A | 8/1995 | Pohndorf et al. |
| 5,456,699 A | 10/1995 | Armstrong |
| 5,468,254 A | 11/1995 | Hahn et al. |
| 5,476,493 A | 12/1995 | Muff |
| 5,509,924 A | 4/1996 | Paspa et al. |
| 5,534,018 A | 7/1996 | Wahlstrand et al. |
| 5,534,022 A | 7/1996 | Hoffmann et al. |
| 5,601,607 A | 2/1997 | Adams |
| 5,603,732 A | 2/1997 | Dahl et al. |
| 5,613,953 A | 3/1997 | Pohndorf |
| 5,690,648 A | 11/1997 | Fogarty et al. |
| 5,721,597 A | 2/1998 | Kakinuma et al. |
| 5,800,465 A * | 9/1998 | Thompson ............ A61N 1/3712 607/9 |
| 5,944,732 A | 8/1999 | Raulerson et al. |
| 5,951,518 A | 9/1999 | Licata et al. |
| 5,951,593 A | 9/1999 | Lu et al. |
| 6,032,079 A | 2/2000 | Ken Knight et al. |
| 6,040,082 A | 3/2000 | Haas et al. |
| 6,059,750 A | 5/2000 | Fogarty et al. |
| 6,091,989 A | 7/2000 | Swerdlow et al. |
| 6,095,987 A | 8/2000 | Shmulewitz et al. |
| 6,104,957 A | 8/2000 | Ala et al. |
| 6,120,431 A * | 9/2000 | Magovern ............ A61M 60/515 623/3.1 |
| 6,122,552 A | 9/2000 | Tockman et al. |
| 6,129,431 A | 10/2000 | Hansen, Jr. et al. |
| 6,159,198 A | 12/2000 | Gardeski et al. |
| 6,228,052 B1 | 5/2001 | Pohndorf |
| 6,324,414 B1 | 11/2001 | Gibbons et al. |
| 6,415,187 B1 | 7/2002 | Kuzma et al. |
| 6,445,954 B1 | 9/2002 | Olive et al. |
| 6,544,247 B1 | 4/2003 | Gardeski et al. |
| 6,721,597 B1 | 4/2004 | Bardy et al. |
| 6,730,083 B2 | 5/2004 | Freigang et al. |
| 6,733,500 B2 | 5/2004 | Kelley et al. |
| 6,749,574 B2 | 6/2004 | O'Keefe |
| 6,770,070 B1 | 8/2004 | Balbierz |
| 6,772,014 B2 | 8/2004 | Coe et al. |
| 6,836,687 B2 | 12/2004 | Kelley et al. |
| 6,856,835 B2 | 2/2005 | Bardy et al. |
| 6,866,044 B2 | 3/2005 | Bardy et al. |
| 6,868,291 B1 | 3/2005 | Bonner et al. |
| 6,887,229 B1 | 5/2005 | Kurth |
| 6,890,295 B2 | 5/2005 | Michels et al. |
| 6,999,819 B2 | 2/2006 | Swoyer et al. |
| 7,033,326 B1 | 4/2006 | Pianca et al. |
| 7,050,851 B2 | 5/2006 | Plombon et al. |
| 7,069,083 B2 | 6/2006 | Finch et al. |
| 7,096,064 B2 | 8/2006 | Deno et al. |
| 7,117,039 B2 | 10/2006 | Manning et al. |
| 7,195,637 B2 | 3/2007 | Mika |
| 7,218,970 B2 | 5/2007 | Ley et al. |
| 7,225,034 B2 | 5/2007 | Ries et al. |
| 7,229,450 B1 | 6/2007 | Chitre et al. |
| 7,272,448 B1 | 9/2007 | Morgan et al. |
| 7,288,096 B2 | 10/2007 | Chin |
| 7,316,667 B2 | 1/2008 | Lindstrom et al. |
| 7,322,960 B2 | 1/2008 | Yamamoto et al. |
| 7,369,899 B2 | 5/2008 | Malinowski et al. |
| 7,389,134 B1 | 6/2008 | Karicherla et al. |
| 7,392,085 B2 | 6/2008 | Warren et al. |
| 7,450,997 B1 | 11/2008 | Pianca et al. |
| 7,496,408 B2 | 2/2009 | Ghanem et al. |
| 7,499,758 B2 | 3/2009 | Cates et al. |
| 7,539,542 B1 | 5/2009 | Malinowski |
| 7,627,375 B2 | 12/2009 | Bardy et al. |
| 7,655,014 B2 | 2/2010 | Ko et al. |
| 7,684,864 B2 | 3/2010 | Olson et al. |
| 7,736,330 B2 | 6/2010 | Bardy |
| 7,761,150 B2 | 7/2010 | Ghanem et al. |
| 7,765,014 B2 | 7/2010 | Eversull et al. |
| 7,801,622 B2 | 9/2010 | Camps et al. |
| 7,837,671 B2 | 11/2010 | Eversull et al. |
| 7,846,088 B2 | 12/2010 | Ness |
| 7,850,610 B2 | 12/2010 | Ferek-Petric |
| 7,890,191 B2 | 2/2011 | Rutten et al. |
| 7,908,015 B2 | 3/2011 | Lazeroms et al. |
| 7,920,915 B2 | 4/2011 | Mann et al. |
| 7,930,028 B2 | 4/2011 | Lang et al. |
| 7,930,040 B1 | 4/2011 | Kelsch et al. |
| 7,983,765 B1 | 7/2011 | Doan et al. |
| 8,060,207 B2 | 11/2011 | Wallace et al. |
| 8,065,020 B2 | 11/2011 | Ley et al. |
| 8,066,702 B2 | 11/2011 | Rittman, III et al. |
| 8,090,451 B2 | 1/2012 | Tyson, Jr. |
| 8,155,755 B2 | 4/2012 | Flynn et al. |
| 8,157,813 B2 | 4/2012 | Ko et al. |
| 8,165,696 B2 | 4/2012 | McClure et al. |
| 8,260,436 B2 | 9/2012 | Gerber et al. |
| 8,280,527 B2 | 10/2012 | Eckerdal et al. |
| 8,340,779 B2 | 12/2012 | Harris et al. |
| 8,355,786 B2 | 1/2013 | Malinowski |
| 8,386,052 B2 | 2/2013 | Harris et al. |
| 8,394,079 B2 | 3/2013 | Drake et al. |
| 8,435,208 B2 | 5/2013 | Bardy |
| 8,442,620 B2 | 5/2013 | Silipo et al. |
| 8,452,421 B2 | 5/2013 | Thenuwara et al. |
| 8,478,424 B2 | 7/2013 | Tronnes |
| 8,478,426 B2 | 7/2013 | Barker |
| 8,594,809 B2 | 11/2013 | Yang et al. |
| 8,686,052 B2 | 4/2014 | Niitsu et al. |
| 8,886,311 B2 | 11/2014 | Anderson et al. |
| 9,126,031 B2 | 9/2015 | Tekmen et al. |
| 9,717,923 B2 | 8/2017 | Thompson-Nauman et al. |

(56) References Cited

U.S. PATENT DOCUMENTS

| | | |
|---|---|---|
| 10,471,267 B2 | 11/2019 | Thompson-Nauman et al. |
| 10,525,272 B2 | 1/2020 | Thompson-Nauman et al. |
| 10,532,203 B2 | 1/2020 | Thompson-Nauman et al. |
| 10,556,117 B2 | 2/2020 | Thompson-Nauman et al. |
| 10,668,702 B2 | 6/2020 | Yang et al. |
| 10,688,270 B2 | 6/2020 | Sims et al. |
| 2002/0049476 A1 | 4/2002 | Bardy et al. |
| 2002/0120294 A1 | 8/2002 | Kroll |
| 2003/0088278 A1 | 5/2003 | Bardy et al. |
| 2003/0114908 A1 | 6/2003 | Flach |
| 2004/0059348 A1 | 3/2004 | Geske et al. |
| 2004/0102829 A1 | 5/2004 | Bonner et al. |
| 2004/0143284 A1 | 7/2004 | Chin |
| 2004/0210293 A1 | 10/2004 | Bardy et al. |
| 2004/0215240 A1 | 10/2004 | Lovett et al. |
| 2004/0215308 A1 | 10/2004 | Bardy et al. |
| 2004/0230279 A1 | 11/2004 | Cates et al. |
| 2004/0230280 A1 | 11/2004 | Cates et al. |
| 2004/0230281 A1 | 11/2004 | Heil et al. |
| 2004/0230282 A1 | 11/2004 | Cates et al. |
| 2004/0236396 A1 | 11/2004 | Coe et al. |
| 2005/0049663 A1 | 3/2005 | Harris et al. |
| 2005/0131505 A1 | 6/2005 | Yokoyama |
| 2005/0277990 A1 | 12/2005 | Ostroff et al. |
| 2005/0288758 A1 | 12/2005 | Jones et al. |
| 2006/0041295 A1 | 2/2006 | Okypka |
| 2006/0116746 A1 | 6/2006 | Chin |
| 2006/0122676 A1 | 6/2006 | Ko et al. |
| 2006/0136004 A1 | 6/2006 | Cowan et al. |
| 2006/0161205 A1 | 7/2006 | Mitrani et al. |
| 2006/0247753 A1 | 11/2006 | Wenger et al. |
| 2006/0253181 A1 | 11/2006 | Schulman et al. |
| 2006/0265018 A1 | 11/2006 | Smith et al. |
| 2007/0023947 A1 | 2/2007 | Ludwig et al. |
| 2007/0049975 A1 | 3/2007 | Cates et al. |
| 2007/0088394 A1 | 4/2007 | Jacobson |
| 2007/0100409 A1 | 5/2007 | Worley et al. |
| 2007/0179388 A1 | 8/2007 | Larik et al. |
| 2007/0208402 A1 | 9/2007 | Helland et al. |
| 2007/0249992 A1 | 10/2007 | Bardy |
| 2008/0046056 A1 | 2/2008 | O—Connor |
| 2008/0243219 A1 | 10/2008 | Malinowski et al. |
| 2008/0269716 A1 | 10/2008 | Bonde et al. |
| 2009/0157091 A1 | 6/2009 | Buysman |
| 2009/0222021 A1 | 9/2009 | Chang |
| 2009/0259283 A1 | 10/2009 | Brandt et al. |
| 2009/0264780 A1 | 10/2009 | Schilling |
| 2009/0270962 A1 | 10/2009 | Yang et al. |
| 2010/0016935 A1 | 1/2010 | Strandberg et al. |
| 2010/0030227 A1 | 2/2010 | Kast et al. |
| 2010/0030228 A1 | 2/2010 | Havel |
| 2010/0042108 A1 | 2/2010 | Hibino |
| 2010/0056858 A1 | 3/2010 | Mokelke et al. |
| 2010/0094252 A1 | 4/2010 | Wengreen et al. |
| 2010/0113963 A1 | 5/2010 | Smits et al. |
| 2010/0125194 A1 | 5/2010 | Bonner et al. |
| 2010/0137879 A1 | 6/2010 | Ko et al. |
| 2010/0152747 A1 | 6/2010 | Padiy et al. |
| 2010/0152798 A1 | 6/2010 | Sanghera et al. |
| 2010/0211064 A1 | 8/2010 | Mahapatra et al. |
| 2010/0217298 A1 | 8/2010 | Bardy |
| 2010/0217301 A1 | 8/2010 | Bardy |
| 2010/0241185 A1 | 9/2010 | Mahapatra et al. |
| 2010/0249696 A1 | 9/2010 | Bardy |
| 2010/0305428 A1 | 12/2010 | Bonner et al. |
| 2010/0318098 A1 | 12/2010 | Lund et al. |
| 2011/0009933 A1 | 1/2011 | Barker |
| 2011/0077708 A1 | 3/2011 | Ostroff |
| 2011/0125163 A1 | 5/2011 | Rutten et al. |
| 2011/0224680 A1 | 9/2011 | Barker |
| 2011/0224681 A1 | 9/2011 | McDonald |
| 2011/0257660 A1 | 10/2011 | Jones et al. |
| 2012/0016377 A1 | 1/2012 | Geroy |
| 2012/0029335 A1 | 2/2012 | Sudam et al. |
| 2012/0078266 A1 | 3/2012 | Tyson, Jr. |
| 2012/0089153 A1 | 4/2012 | Christopherson et al. |
| 2012/0097174 A1 | 4/2012 | Spotnitz et al. |
| 2012/0123496 A1 | 5/2012 | Schotzko et al. |
| 2012/0191106 A1 | 7/2012 | Ko et al. |
| 2012/0209283 A1 | 8/2012 | Zhu |
| 2012/0209285 A1 | 8/2012 | Barker et al. |
| 2012/0209286 A1 | 8/2012 | Papay et al. |
| 2012/0220849 A1 | 8/2012 | Brockway et al. |
| 2012/0316613 A1 | 12/2012 | Keefe et al. |
| 2013/0041345 A1 | 2/2013 | Kilcoin et al. |
| 2013/0103049 A1 | 4/2013 | Bonde |
| 2013/0158564 A1 | 6/2013 | Harris et al. |
| 2013/0238067 A1 | 9/2013 | Baudino |
| 2014/0330325 A1 | 11/2014 | Thompson-Nauman et al. |
| 2014/0330326 A1 | 11/2014 | Thompson-Nauman et al. |
| 2014/0330327 A1 | 11/2014 | Thompson-Nauman et al. |
| 2014/0330329 A1 | 11/2014 | Thompson-Nauman et al. |
| 2014/0330331 A1 | 11/2014 | Thompson-Nauman et al. |
| 2020/0069952 A1 | 3/2020 | Thompson-Nauman et al. |
| 2020/0129755 A1 | 4/2020 | Thompson-Nauman et al. |
| 2020/0289816 A1 | 9/2020 | Thompson-Nauman et al. |
| 2022/0249835 A1 | 8/2022 | Thompson-Nauman |
| 2022/0249855 A1 | 8/2022 | Thompson-Nauman et al. |

FOREIGN PATENT DOCUMENTS

| | | |
|---|---|---|
| EP | 0347353 A1 | 12/1989 |
| EP | 1541191 | 6/2005 |
| FR | 2773491 A1 | 7/1999 |
| JP | 2007500549 A | 1/2007 |
| WO | 9938568 A1 | 8/1999 |
| WO | WO 2001023035 A1 | 4/2001 |
| WO | 02242275 A2 | 3/2002 |
| WO | WO 0226315 A1 | 4/2002 |
| WO | 0241946 A2 | 5/2002 |
| WO | WO 2004073506 A2 | 9/2004 |
| WO | WO 2005011809 A2 | 2/2005 |
| WO | 2006060705 A1 | 6/2006 |
| WO | WO 20100047893 A1 | 4/2010 |

OTHER PUBLICATIONS

Office Action, in the Chinese language, from Chinese Application No. 201480025740.9, dated Sep. 27, 2016, 9 pp.

First Office Action and Search Report, and translation thereof, from counterpart Chinese Application No. 201480035082.1, dated Sep. 27, 2016, 29 pp.

First Office Action and Search Report, and translation thereof, from counterpart Chinese Application No. 201480025657.1, dated Oct. 8, 2016, 24 pp.

(PCT/US2014/036760) PCT Notification of Transmittal of the International Search Report and the Written Opinion of the International Searching Authority, dated Jul. 29, 2014, 11 pages.

Prosecution History of Opposition from European Patent No. 1318856, dated Apr. 15, 2015 through Apr. 10, 2017, 312 pp.

Bardy et al., "An Entirely Subcutaneous Implantable Cardioverter-Defibrillator," The New England Journal of Medicine, May 2010, 9 pp.

Bardy et al., "A Simplified, Single-Lead Unipolar Transvenous Cardioversion-Defibrillation System," Circulation, vol. 8, No. 2, Aug. 1993, 5 pp.

"Pharmacological and Electrical Cardioversion of AF," Europace Supplements, vol. 2, Jan. 2001, 1 pp.

Boston Scientific, "Dr. Lucas Boersma Shares Insight into the S-ICD Effortless 3-year Analysis," retrieved from http://www.bostonscientific.com/en-EU/products/defibrillators/s-icd-emblem/clinical-data.html on Nov. 24, 2016, 3 pp.

Bocker et al., "Treatment with implantable defibrillators in childhood," Herzschr Elektrophys, accepted Nov. 11, 1999, 4 pp.

"Emblem S-ICD, Emblem MRI S-ICD," Boston Scientific, REF 4209, A219, Manual 359481-001, Nov. 2015, 72 pp.

Thogersen et al., "Implantable Cardioverter Defibrillator in a 4-Month-Old Infant with Cardiac Arrest Associated with a Vascular Heart Tumor," accepted Jan. 8, 2001, Pace, vol. 24, Nov. 2001, 2 pp.

(56) References Cited

OTHER PUBLICATIONS

"St. Jude Medical Announces Filing of PMA Supplement for Ventritex Angstrom MD and Contour MD ICD's," St. Jude Medical, Inc., Jun. 5, 1998, 1 pp.

Fischbach et al., "Use a Single Coil Transvenous Electrode with an Abdominally Placed Implantable Cardioverter Defibrillator in Children," Place, vol. 23, May 2000, 5 pp.

Gradaus et al., "Nonthoracotomy Implantable Cardioverter Defibrillator Placement in Children: Use of Subcutaneous Array Leads and Abdominally Placed Implantable Cardioverter Defibrillators in Children," Journal of Cardiovascular Electrophysiology, vol. 12, No. 3, Mar. 2001, 5 pp.

Haffajee et al., "A Multicenter, Randomized Trial Comparing an Active Can Implantable Defibrillator with a Passive Can System" Pace, vol. 20, Jan. 1997, Part II, 5 pp.

Hoffmann et al., "experience with pectoral versus abdominal implantation of a small defibrillator," European Heart Journal, vol. 19, Jul. 1998, 14 pp.

Juchem et al., "Successful use of transvenous coil electrodes as single element subcutaneous array leads," published online Jan. 14, 2009, 4 pp.

Kriebel et al., "Implantation of an 'extracardiac' internal cardioverter defibrillator in a 6-month-old infant," Zeitschrift fur Kardiologie, Jan. 18, 2005, 4 pp.

Kuschyk et al., "A Multcenter Study of Shock Pathways for Subcutaneous Implantable Defibrillators," Journal of Cardiovascular Electrophysiology, vol. 25, No. 1, Jan. 2014, 7 pp.

Olson et al., "Onset and Stability for Ventricular Tachyarrhythmia Detection in an Implantable Pacer-Cardioverter-Defibrillator," IEEE, 1987, 4 pp. (Applicant points out, in accordance with MPEP 609.04(a), that the year of publication, 1987, is sufficiently earlier than the effective U.S. filing date, so that the particular month of publication is not in issue.).

Park et al., "Use of an Implantable Cardioverter Defibrillator in an Eight-Moth-Old Infant with Ventricular Fibrillation Arising from a Myocardial Fibroma," Pace, vol. 22, Jan. 1999, Part I, 2 pp.

Schuder et al., "Ventricular Defibrillation in the Dog Using Implanted and Partially Implanted Electrode Systems," The American Journal of Cardiology, vol. 33, Feb. 1974, 5 pp.

Schuder et al., "Experimental Ventricular Defibrillation with an Automatic and Completely Implanted System," Trans. Amer. Soc. Artif. Int. Organs, vol. XVI, 1970, (Applicant points out, in accordance with MPEP 609.04(a), that the year of publication, 1970, is sufficiently earlier than the effective U.S. filing date, so that the particular month of publication is not in issue.).

Schuder, "The Role of an Engineering Oriented Medical Research Group in Developing Improved Methods ad Devices for Achieving Ventricular Defibrillation The University of Missouri Experience," Pace, vol. 16, Jan. 1993, 30 pp.

Weiss et al., Safety and Efficacy of a Totally Subcutaneous Implantable-Cardioverter Defibrillator, Arrhythmia/Electrophysiology, Jun. 28, 2013, 11 pp.

Office Action from U.S. Appl. No. 16/725,458, dated Jun. 25, 2021, 6 pp.

Office Action from U.S. Appl. No. 16/678,365, dated Jun. 25, 2021, 6 pp.

"SQ-RX Pulse Generator, A Component of the S-ICD System," User's Manual, Model 1010, Cameron Health, Inc., Dec. 2, 2008, 46 pp.

Alexander et al., "Implications of Implantable Cardioverter Defibrillator Therapy in Congenital Heart Disease and Pediatrics," Journal of Cardiovascular Electrophysiology, vol. 15, No. 1, Jan. 2004, 5 pages.

Avogadros Lab Supply Inc., Catalog; Scoopula with Beech Wood Handle, can be found on-line at http://www. avogadro-lab-supply. com/search.php, accessed Oct. 6, 2013, 1 page.

Baddour et al., Update on Cardiovascular Implantable Electronic Device Infections and their Management—A Scientific Statement from the American Heart Association, Circulation available at http://circ.ahajournals.org, Jan. 26, 2010, 23 pages.

Baudoin et al., "The Superior Epigastric Artery Does Not Pass Through Larrey's Space (Trigonum Sternocostale)" Surgical Radial Anal (2003), 25: 259-262.

Bauersfeld et al., "Initial Experience with Implantable Cardioverter Defibrillator Systems Using Epicardial and Pleural Electrodes in Pediatric Patients," The Annals of Thoracic Surgery, 2007, vol. 84, 3 pages.

Berul et al., "Minimally Invasive Cardioverter Defibrillator Implantation for Children: An Animal Model and Pediatric Case Report," Journal of Pacing and Clinical Electrophysiology, Dec. 2001, vol. 24, No. 12, 6 pages.

Bielefeld et al., "Thoracoscopic Placement of Implantable Cardioverter-Defibrillator Patch Leads in Sheep", Circulation; Nov. 1993, vol. 88, No. 5, Part 2; 5 pages.

Bolling et al., "Automatic Internal Cardioverter Defibrillator: A Bridge to Heart Transplantation", Heart Lung Transplantation, Abstract Only, Jul.-Aug. 1991, 1 page.

Cigna et al., "A New Technique for Substernal Colon Transposition with A Breast Dissector: Report of 39 Cases", Journal of Plastic, Reconstructive and Aesthetic Surgery, 2006:59, 4 pages.

Copper, et al., "Implantable Cardioverter Defibrillator Lead Complications and Laser Extraction in Children and Young Adults with Congenital Heart Disease: Implications for Implantation and Management," Journal of Cardiovascular Electrophysiology, vol. 14, No. 4, Apr. 2003, 7 pages.

Damiano, "Implantation of Cardioverter Defibrillators in the Post-Sternotomy Patient", The Annals of Thoracic Surgery, 1992; 53: pp. 978-983.

Ely et al., "Thoracoscopic Implantation of the Implantable Cardioverter Defibrillator"; Minimally Invasive Techniques; (Can be found on the World-Wide Web at http://chestioumal.chestpubs.org on May 6; 2013); dated Jan. 1993; 2 pages.

Erickson, MD., "Non-thoracotomy ICD Implantation in Pediatric and Adult Congenital Heart Disease Patients," Oct. 2015, 44 slides.

Falk et al., "External Cardiac Pacing Using Low Impedance Electrodes Suitable for Defibrillation: A Comparative Blinded Study," Journal of American College of Cardiology, vol. 22, No. 5, Nov. 1, 1993,5 pages.

Frame et al., "Long-Term Stability of Defibrillation Thresholds with Intrapericardial Defibrillator Patches", Pacing and Clinical Electrophysiology, Jan. 1993, Part II, vol. 16, 6 pages.

Ganapathy et al., ""Implantable Device to Monitor Cardiac Activity with Sternal Wires,"" Pace, vol. 37, Dec. 2014, 11 pages.

Guenther et al., ""Substernal Lead Implantation: A Novel Option to Manage OFT Failure in S-ICD patients,"" Clinical Research Cardiology, Published On-line Oct. 2, 2014, 3 pages.

Harman et al., "Differences in the Pathological Changes in Dogs' Hearts After Defibrillation with Extrapericardial Paddles and Implanted Defibrillator Electrodes", Journal of Pacing and Clinical Electrophysiology, Feb. 1991; vol. 14; Part 2; 5 pages.

Haydin et al., "Subxiphoid Approach to Epicardial Implantation of Implantable Cardioverter Defibrillators in Children", PACE, vol. 36, Aug. 2013, 5 pages.

Hsia et al., "Novel Minimally Invasive, Intrapericardial Implantable Cardioverter Defibrillator Coil System: A Useful Approach to Arrhythmia Therapy in Children," The Annals of Thoracic Surgery, 2009, vol. 87, 6 pages.

Karwande et al., "Bilateral Anterior Thoracotomy for Automatic Implantable Cardioverter Defibrillator Placement in Patients with Previous Sternotomy"; The Annals of Thoracic Surgery; Oct. 1992; 54(4); 3 pages.

Laudon, M. K., "Pulse Output", Chapter 11 of Design of Pacemakers, Published by the Institute of Electrical and Electronics Engineers, Inc., New York,(1995), 30 pages.

Lawrie et al., "Right Mini-Thoracotomy: An Adjunct to Left Subcostal Automatic Implantable Cardioverter Defibrillator Implantation", The Annals of Thoracic Surgery; 1989; 47; 4 pages.

Lemmer, "Defibrillator Patch Constriction, Letter to the Editor", The Annals of Thoracic Surgery, 1996, 1 page.

Medtronic, Inc. 6996SQ Subcutaneous, Unipolar Lead with Defibrillation Coil Electrode, Technical Manual, 22 pages.

Medtronic, Inc. 6996T Tunneling Tool, Technical Manual, 12 pages.

(56) References Cited

OTHER PUBLICATIONS

Mitchell et al., "Experience with an Implantable Tiered Therapy Device Incorporating Antitachycardia Pacing and Cardioverter/Defibrillator Therapy", Thoracic and Cardiovascular Surgery, Abstract Only, Mar. 1993, 1 page.
Molina et al, "An Epicardial Subxiphoid Implantable Defibrillator Lead: Superior Effectiveness After Failure of Standard Implants", From the Department of Surgery, Division of Cardiovascular and Thoracic Surgery and the Department of Medicine, Cardiac Arrhythmia Center, University of Minnesota Medical School, Minneapolis, Minnesota, Pace, vol. 27, Nov. 2004, 7 pages.
Obadia et al., "Thoracoscopic Approach to Implantable Cardioverter Defibrillator Patch Electrode Implantation", Pacing and Clinical Electrophysiology; Jun. 1996; vol. 19; 6 pages.
Obadia, et al., "New Approach for Implantation of Automatic Defibrillators Using Videothoracoscopy", Journal Ann Cardiel Angeiol (Paris); Sep. 1994; 43 (7) Abstract Only, 1 page.
Pebax Product Brochure, 14 pages and can be found on-line at http://www.pebax.com/export/sites/pebax/.content/medias/downloads/literature/pebax-product-range-brochure.pdf, 14 pages.
Piccione, et al., "Erosion of Extrapericardial Implantable Cardioverter Defibrillator Patch Through the Gastric Fundus with Fistulous Tract Information", Cardiology in Review; 2006; 14, e21-e23 pages.
Quigley et al., "Migration of an Automatic Implantable Cardioverter-Defibrillator Patch Causing Massive Hemothorax", Journal Texas Heart Institute, Nov. 1, 1996; vol. 23, 4 pages.
Sgoifo et al., "Electrode Positioning for Reliable Telemetry ECG Recordings During Social Stress in Unrestrained Rats," Physiology and Behaviors, vol. 60, issue 6, Dec. 1996, pp. 1397-1401.
Shapira, et al., "A Simplified Method for Implantation of Automatic Cardioverter Defibrillator in Patients with Previous Cardiac Surgery", Pacing and Clinical Electrophysiology, January Part I, 1993, vol. 16; 6 pages.
Steinke et al., "Subepicardial Infarction, Myocardial Impression, and Ventricular Penetration by Sutureless Electrode and Leads", Chest; 70: 1, Jul. 1976, 2 pages.
Thompson-Nauman et al., "Implantable Cardioverter-Defibrillator (ICD) System Including Substernal Packing Lead," Notice of Third Office Action, Chinese Patent Application No. 201480035082.1, Dispatched Jan. 2, 2018, 22 pages.
Thompson-Nauman et al., "Implantable Cardioverter-Defibrillator (ICD) System Including Substernal Lead," Notice of Third Of Office Action, Chinese Patent Application No. 201480025740.9, Dispatched Jan. 2, 2018, 19 pages.
Thompson-Nauman et al., "Implantable Cardioverter-Defibrillator (ICD) System Including Substernal Lead," JP Patent Application No. 2016-512987, Japanese Office Action dated Feb. 2, 2018, 4 pages.
Tung et al., ""Initial Experience of Minimal Invasive Extra Cardiac Placement Of High Voltage Defibrillator Leads, "" Canadian Cardiovascular Congress 2007, Oct. 2007, vol. 23, Supplement SC, Abstract 0697, http://www.pulsus.com/ccc2007/abs/0697.htm, 2 pages.
Tung et al., "Minimal Invasive Extra Cardiac Placement of High Voltage Defibrillator Leads", Poster 3; S200 Abstract, P0-3-4; St. Paul Hospital, Vancouver, British Columbia, Canada, 1 page.
Tung, et al. "Invention Disclosure Form for Hybrid Endovascular and Extravascular Implantable Cardioverter-Defibrillator System," Mar. 2006, 10 pages.
Vyhmeister et al., "Simple Approach for Extrapericardial Placement of Defibrillator Patches Via Median Sternotomy", The Annals of Thoracic Surgery; 1994; 57:4 pages.
U.S. Appl. No. 16/725,458, filed Dec. 23, 2019 by Thompson-Nauman et al.
Prosecution History from U.S. Appl. No. 14/261,470, dated Apr. 25, 2014 through Oct. 3, 2019, 219 pp.
Prosecution History from U.S. Appl. No. 16/678,365, dated Nov. 8, 2019 through Jan. 10, 2020, 32 pp.
Prosecution History from U.S. Appl. No. 14/261,488, dated Apr. 25, 2014 through Jan. 27, 2020, 300 pp.
Prosecution History from U.S. Appl. No. 14/261,456, dated Apr. 25, 2014 through Dec. 12, 2019, 220 pp.
Prosecution History from U.S. Appl. No. 14/261,460, dated Apr. 25, 2014 through May 11, 2017, 61 pp.
Prosecution History from U.S. Appl. No. 15/661,365, dated Jul. 27, 2017 through Dec. 9, 2019, 139 pp.
Prosecution History from U.S. Appl. No. 14/261,479, dated Apr. 25, 2014 through Dec. 12, 2019, 199 pp.
Thompson-Nauman et al., Implantable Cardioverter-Defibrillator (ICD) System Including Substernal Pacing Lead, Notice of Third Office Action, Chinese Patent Application No. 201480025657.1, Dispatched Jan. 2, 2018, 20 pages.
Notice of Allowance from U.S. Appl. No. 16/678,365, dated Feb. 23, 2022, 2 pp.
Notice of Allowance from U.S. Appl. No. 16/678,365, dated Jan. 26, 2022, 5 pp.
Notice of Allowance from U.S. Appl. No. 16/725,458, dated Jan. 28, 2022, 5 pp.
Office Action from U.S. Appl. No. 16/885,837, dated Dec. 24, 2021, 7 pp.
Response to Office Action dated Dec. 24, 2021, from U.S. Appl. No. 16/885,837, filed Mar. 24, 2022, 3 pp.
Response to Office Action dated Jun. 25, 2021, from U.S. Appl. No. 16/678,365, filed Sep. 27, 2021, 9 pp.
Response to Office Action dated Jun. 25, 2021, from U.S. Appl. No. 16/725,458, filed Sep. 27, 2021, 14 pp.
Corrected Notice of Allowability from U.S. Appl. No. 16/885,837, dated May 4, 2022, 2 pp.
Notice of Allowance from U.S. Appl. No. 16/885,837, dated May 13, 2022, 5 pp.
Notice of Allowance from U.S. Appl. No. 16/885,837, dated Apr. 12, 2022, 5 pp.
U.S. Appl. No. 17/930,994, filed Sep. 9, 2022, naming inventors Thompson-Nauman et al.
Prosecution History from U.S. Appl. No. 16/885,837, dated Jun. 17, 2020 through Nov. 15, 2022, 32 pp.

* cited by examiner

IMPLANTABLE CARDIOVERTER-DEFIBRILLATOR (ICD) SYSTEM INCLUDING SUBSTERNAL PACING LEAD

This application is a divisional of U.S. application Ser. No. 14/261,456, filed Apr. 25, 2014, which claims the benefit of U.S. Provisional Application No. 61/819,866, filed on May 6, 2013 and U.S. Provisional Application No. 61/819,984, filed on May 6, 2013. The entire content of each of the applications is incorporated herein by reference.

FIELD OF THE INVENTION

The present application relates to methods and medical devices for providing an implantable cardiac defibrillation system including a substernal pacing lead.

BACKGROUND OF THE INVENTION

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients at high risk of ventricular fibrillation, the use of an implantable cardioverter defibrillator (ICD) system has been shown to be beneficial at preventing SCD. An ICD system includes an ICD, which is a battery powered electrical shock device, that may include an electrical housing electrode (sometimes referred to as a can electrode), that is coupled to one or more electrical lead wires placed within the heart. If an arrhythmia is sensed, the ICD may send a pulse via the electrical lead wires to shock the heart and restore its normal rhythm. Owing to the inherent surgical risks in attaching and replacing electrical leads directly within or on the heart, subcutaneous ICD systems have been devised to provide shocks to the heart without placing electrical lead wires within the heart or attaching electrical wires directly to the heart.

Subcutaneous ICD systems have been devised to deliver shocks to the heart by the use of a defibrillation lead placed subcutaneously on the torso. However, the subcutaneous ICD systems may require an output of around 80 Joules (J) of energy to provide effective defibrillation therapy. As a result, subcutaneous ICDs may require larger batteries and more storage capacitors than transvenous ICDs. As such, the subcutaneous ICDs are generally larger in size than transvenous ICDs. The large size of the subcutaneous ICD may compromise patient comfort, decrease system longevity and/or increase cost of the system. In addition, conventional subcutaneous ICD systems are incapable of delivering anti-tachycardia pacing (ATP) without extreme discomfort to the patient, which is a standard therapy in transvenous ICDs to terminate lethal tachyarrhythmias without providing a shock.

SUMMARY OF THE INVENTION

The present application advantageously provides implantable cardiac systems and methods for providing substernal pacing in an implantable cardiac defibrillation system. In one embodiment, an ICD system comprises an ICD implanted subcutaneously in a patient, a defibrillation lead having a proximal portion coupled to the ICD and a distal portion having a defibrillation electrode configured to deliver a defibrillation shock to a heart of the patient, and a pacing lead that includes a distal portion having one or more electrodes and a proximal portion coupled to the ICD, the distal portion of the pacing lead being implanted at least partially along a posterior side of a sternum of the patient and configured to deliver pacing pulses to the heart of the patient. The ICD is configured to provide pacing pulses to the heart of the patient via the pacing lead and provide defibrillation shocks to the patient via the defibrillation lead.

In another embodiment, a method comprises generating a defibrillation pulse with an implantable cardiac device implanted within a patient, delivering the defibrillation pulse via at least one electrode of a defibrillation lead coupled to the implantable cardiac device, generating one or more pacing pulses with the implantable cardiac device, and delivering the one or more pacing pulses via at least one electrode of a pacing lead coupled to the implantable cardiac device and implanted at least partially along a posterior side of a sternum of the patent.

In a further embodiment, an implantable cardioverter-defibrillator (ICD) system comprising an ICD implanted subcutaneously in a patient, a first lead having a proximal portion coupled to the ICD and a distal portion having one or more electrodes configured to deliver electrical stimulation therapy to a heart of the patient, and a second lead that includes a proximal portion coupled to the ICD and a distal portion having one or more electrodes, the distal portion of the second lead being implanted at least partially along a posterior side of a sternum of the patient. The ICD is configured to sense electrical signals of the heart of the patient using the one or more electrodes of the second lead, detect a tachycardia using the sensed electrical signals, and provide electrical stimulation therapy to the patient using the one or more electrodes of the first lead.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1A:
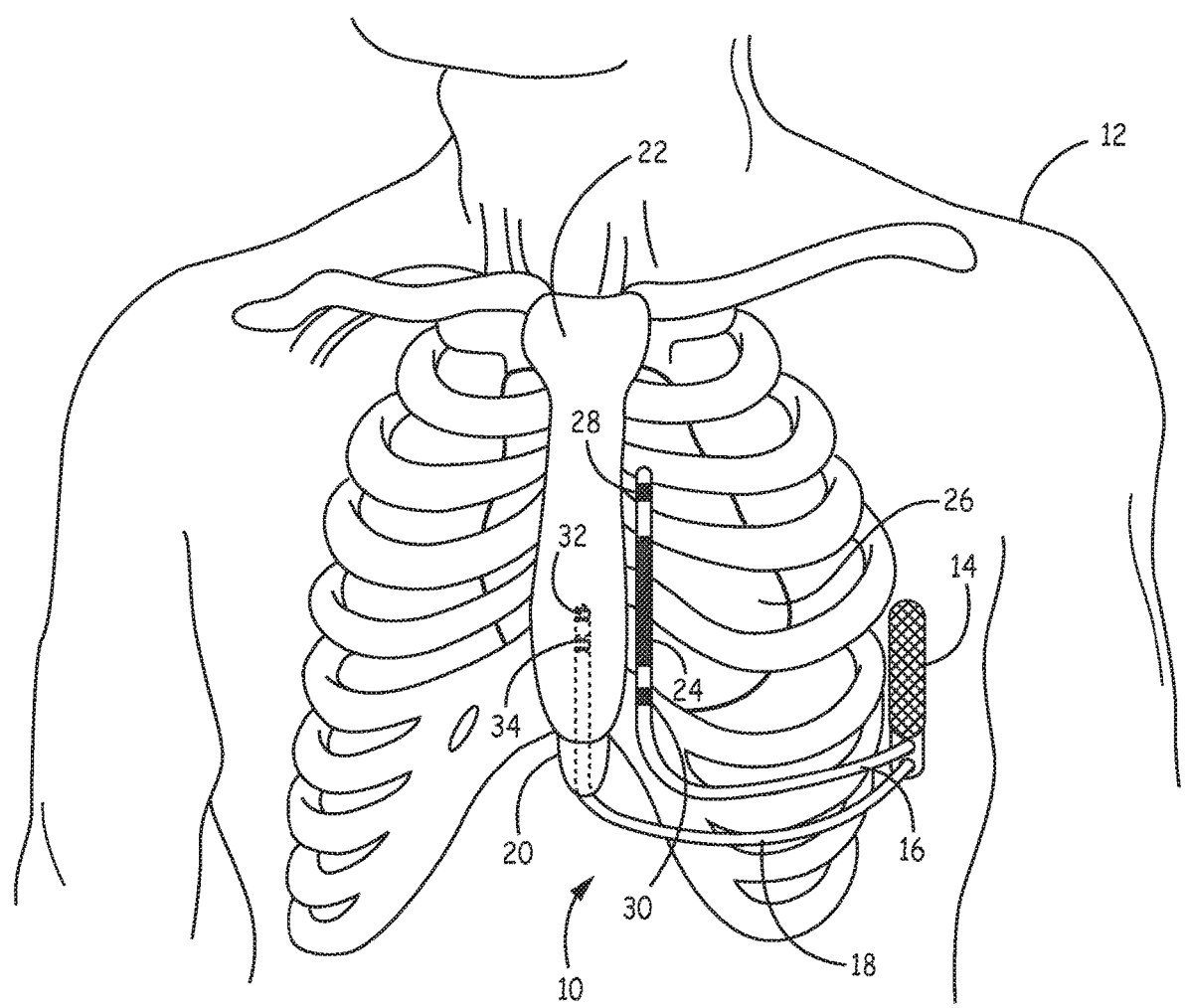
FIG. 1A is a front view of a patient implanted with implantable cardiac system having a substernal pacing lead.
Figure 1B:
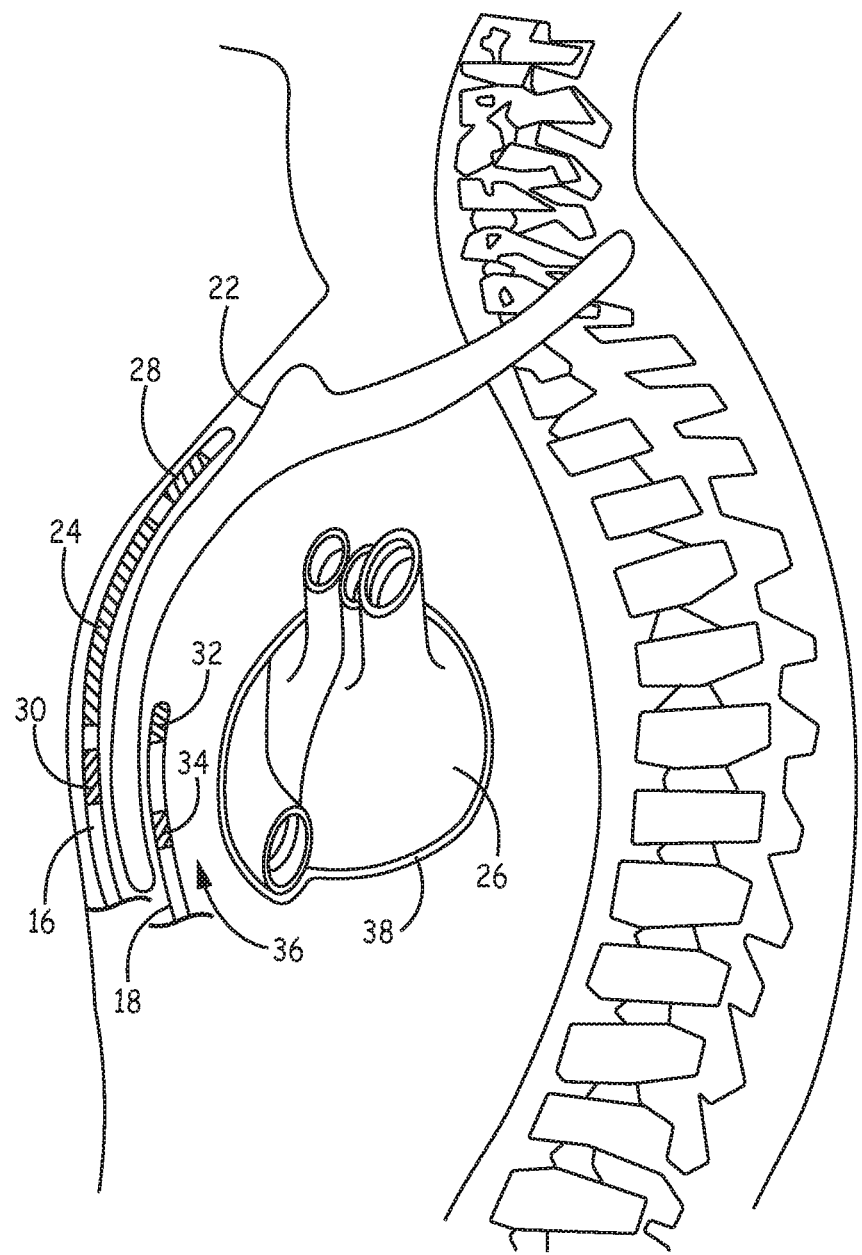
FIG. 1B is a side view of the patient with the implantable cardiac system having a substernal pacing lead.
Figure 1C:
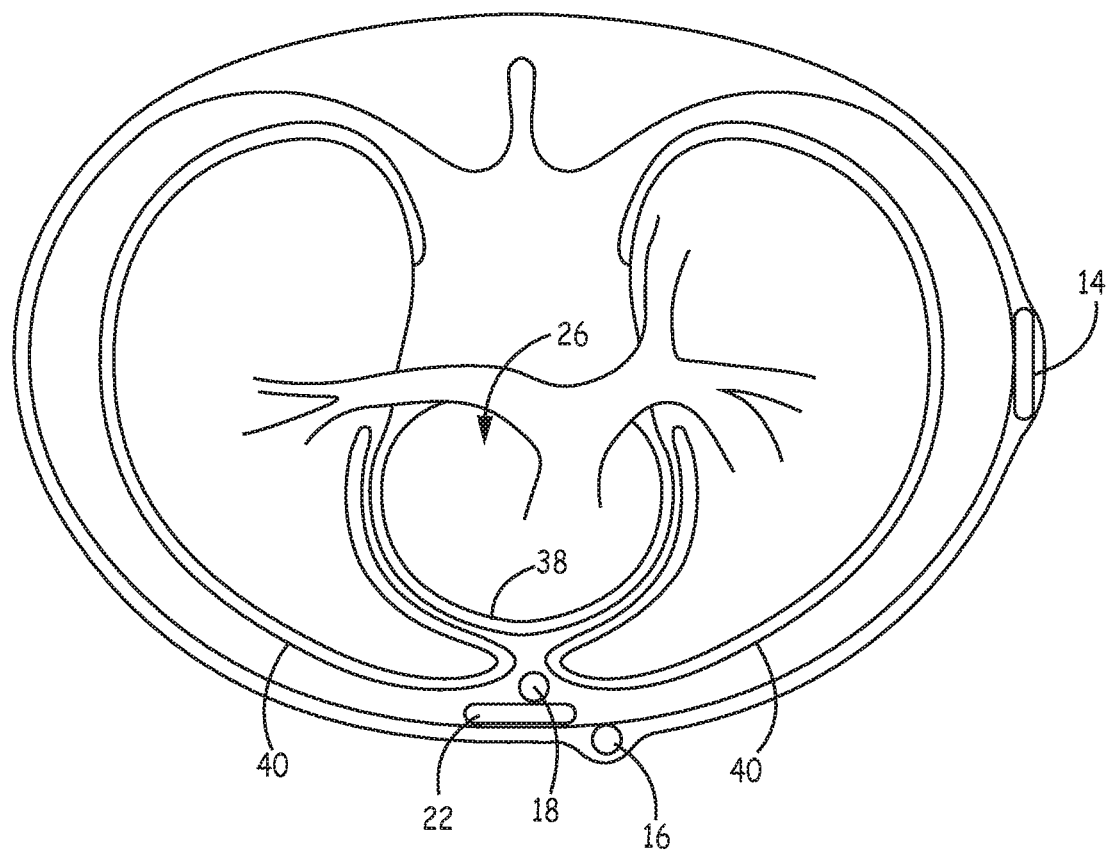
FIG. 1C is a transverse view of the patient with the implantable cardiac system having a substernal pacing lead.

FIGS. 1A-C are conceptual diagrams of an implantable cardiac system 10 implanted within a patient 12. FIG. 1A is a front view of patient 12 implanted with implantable cardiac system 10. FIG. 1B is a side view of patient 12 with implantable cardiac system 10. FIG. 1C is a transverse view of patient 12 with implantable cardiac system 10.

Implantable cardiac system 10 includes an implantable medical device, in this example an ICD 14, connected to a defibrillation lead 16 and a pacing lead 18. In the example illustrated in FIGS. 1A-C, ICD 14 is implanted subcutaneously on the left side of patient 12 above the ribcage. ICD 14 may, in some instances, be implanted between the left posterior axillary line and the left anterior axillary line of patient 12. ICD 14 may, however, be implanted at other subcutaneous locations on patient 12 as described later.

Defibrillation lead 16 includes a proximal end that includes a connector (not shown) configured to be connected to ICD 14 and a distal portion that includes electrodes 24, 28, and 30. Defibrillation lead 16 extends subcutaneously above the ribcage from ICD 14 toward a center of the torso of patient 12, e.g., toward xiphoid process 20 of patient 12. At a location near xiphoid process 20, defibrillation lead 16 bends or turns and extends superior subcutaneously above the ribcage and/or sternum, substantially parallel to sternum 22. Although illustrated in FIGS. 1A-C as being offset laterally from and extending substantially parallel to sternum 22, defibrillation lead 16 may be implanted at other locations, such as over sternum 22, offset to the right of sternum 22, angled lateral from sternum 22 at either the proximal or distal end, or the like.

Defibrillation lead 16 includes a defibrillation electrode 24 toward the distal portion of defibrillation lead 16, e.g., toward the portion of defibrillation lead 16 extending superior near sternum 22. Defibrillation lead 16 is placed along sternum 22 such that a therapy vector between defibrillation electrode 24 and a housing electrode of ICD 14 (or other second electrode of the therapy vector) is substantially across the ventricle(s) of heart 26. The therapy vector may, in one example, be viewed as a line that extends from a point on defibrillation electrode 24, e.g., center of defibrillation electrode 24, to a point on the housing electrode of ICD 14, e.g., center of the housing electrode. In one example, the therapy vector between defibrillation electrode 24 and the housing electrode of ICD 14 (or other second electrode of the therapy vector) is substantially across the right ventricle of heart 26.

Defibrillation electrode 24 is illustrated in FIG. 1 as being an elongated coil electrode. Defibrillation electrode 24 may vary in length depending on a number of variables. Defibrillation electrode 24 may, in one example, have a length of between approximately 5-10 centimeters (cm). However, defibrillation electrode 24 may have a length less than 5 cm and greater than 10 cm in other embodiments. Another example, defibrillation electrode 24 may have a length of approximately 2-16 cm.

In other embodiments, however, defibrillation electrode 24 may be a flat ribbon electrode, paddle electrode, braided or woven electrode, mesh electrode, segmented electrode, directional electrode, patch electrode or other type of electrode besides an elongated coil electrode. In one example, defibrillation electrode 24 may be formed of a first segment and a second segment separated by a distance and having at least one sensing electrode located between the first and second defibrillation electrode segments. In other embodiments, defibrillation lead 16 may include more than one defibrillation electrode. For example, defibrillation lead 16 may include a second defibrillation electrode (e.g., second elongated coil electrode) near a proximal end of lead 16 or near a middle of lead 16.

Defibrillation lead 16 also includes electrodes 28 and 30 located along the distal portion of defibrillation lead 16. In the example illustrated in FIGS. 1A-C, electrode 28 and 30 are separated from one another by defibrillation electrode 24. In other examples, however, electrodes 28 and 30 may be both distal of defibrillation electrode 24 or both proximal of defibrillation electrode 24. In instances in which defibrillation electrode 24 is a segmented electrode with two defibrillation segments, one or both electrodes 28 and 30 may be located between the two segments and, in some cases, lead 16 may include additional electrodes proximal or distal to the defibrillation segments.

Electrodes 28 and 30 may comprise ring electrodes, short coil electrodes, paddle electrodes, hemispherical electrodes, segmented electrodes, directional electrodes, or the like. Electrodes 28 and 30 of lead 16 may have substantially the same outer diameter as the lead body. In one example, electrodes 28 and 30 may have surface areas between 1.6-55 $mm^2$. Electrodes 28 and 30 may, in some instances, have relatively the same surface area or different surface areas. Depending on the configuration of lead 16, electrodes 28 and 30 may be spaced apart by the length of defibrillation electrode 24 plus some insulated length on each side of defibrillation electrode, e.g., approximately 2-16 cm. In other instances, such as when defibrillation 28 and 30 are between a segmented defibrillation electrode, the electrode spacing may be smaller, e.g., less than 2 cm or less than 1 cm. The example dimensions provided above are exemplary in nature and should not be considered limiting of the embodiments described herein. In other embodiments, defibrillation lead 16 may not include electrodes 28 and/or 30. In this case, defibrillation lead 16 would only include defibrillation electrode 24 and sensing may be achieved using sensing electrodes of pacing lead 18, as described further below. Alternatively, defibrillation lead 16 may include more than two pace/sense electrodes.

ICD 14 may obtain sensed electrical signals corresponding with electrical activity of heart 26 via a combination of sensing vectors that include combinations of electrodes 28 and/or 30 and the housing electrode of ICD 14. For example, ICD 14 may obtain electrical signals sensed using a sensing vector between electrodes 28 and 30, obtain electrical signals sensed using a sensing vector between electrode 28 and the conductive housing electrode of ICD 14, obtain electrical signals sensed using a sensing vector between electrode 30 and the conductive housing electrode of ICD 14, or a combination thereof. In some instances, ICD 14 may even obtain sensed electrical signals using a sensing vector that includes defibrillation electrode 24.

Pacing lead 18 includes a proximal end that includes a connector configured to be connected to ICD 14 and a distal portion that includes electrodes 32 and 34. Pacing lead 18 extends subcutaneously above the ribcage from ICD 14 toward the center of the torso of patient 12, e.g., toward xiphoid process 20. At a location near xiphoid process 20, pacing lead 18 bends or turns and extends superior underneath/below sternum 22 in anterior mediastinum 36. Anterior mediastinum 36 may be viewed as being bounded laterally by pleurae 40, posteriorly by pericardium 38, and anteriorly by sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 18 extends along the posterior side of sternum 22 substantially within the loose connective tissue and/or substernal musculature of anterior mediastinum 36. A lead implanted with the distal portion substantially within anterior mediastinum 36 will be referred to herein as a substernal lead. Also, electrical stimulation, such as pacing, provided by a lead implanted with the distal portion substantially within anterior mediastinum 36 will be referred to herein as substernal electrical stimulation or substernal pacing.

Pacing lead 18 is implanted within anterior mediastinum 36 such that electrodes 32 and 34 are located near the ventricle of heart 26. For instance, the distal portion of pacing lead 18 may be implanted substantially within anterior mediastinum 36 such that electrodes 32 and 34 are located over a cardiac silhouette of the ventricle as observed via an anterior-posterior (AP) fluoroscopic view of heart 26. In one example, pacing lead 18 may be implanted such that one or both of a unipolar pacing vector from electrode 32 to a housing electrode of ICD 14 and/or a unipolar pacing vector from electrode 34 to the housing electrode of ICD 14 are substantially across the ventricles of heart 26. The therapy vector may again be viewed as a line that extends from a point on electrode 32 or 34, e.g., center of electrode 32 or 34, to a point on the housing electrode of ICD 14, e.g., center of the housing electrode. In another example, the spacing between electrodes 32 and 34 as well as the placement of pacing lead 18 may be such that a bipolar pacing vector between electrode 32 and electrode 34 is centered or otherwise located over the ventricle. However, pacing lead 18 may be positioned at other locations as long as unipolar and/or bipolar pacing vectors using electrodes 32 and 34 result in capture of the ventricle of the heart.

In the example illustrated in FIGS. 1A-C, pacing lead 18 is located substantially centered under sternum 22. In other instances, however, pacing lead 18 may be implanted such that it is offset laterally from the center of sternum 22. In some instances, pacing lead 18 may extend laterally enough such that all or a portion of the distal portion of pacing lead 18 is underneath/below the ribcage in addition to or instead of sternum 22 while still within the anterior mediastinum 22.

The distal portion of lead 18 is described herein as being implanted substantially within anterior mediastinum 36. Thus, points along the distal portion of lead 18 may extend out of anterior mediastinum 36, but the majority of the distal portion is within anterior mediastinum 36. In other embodiments, the distal portion of lead 18 may be implanted in other non-vascular, extra-pericardial locations, including the gap, tissue, or other anatomical features around the perimeter of and adjacent to, but not attached to, the pericardium or other portion of heart 26 and not above sternum 22 or ribcage. As such, lead 16 may be implanted anywhere within the "substernal space" defined by the undersurface between the sternum and/or ribcage and the body cavity but not including the pericardium or other portion of heart 26. The substernal space may alternatively be referred to by the terms "retrosternal space" or "mediastinum" or "infrasternal" as is known to those skilled in the art and includes the anterior mediastinum 36. The sub sternal space may also include the anatomical region described in Baudoin, Y. P., et al., entitled "The superior epigastric artery does not pass through Larrey's space (trigonum sternocostale)." Surg. Radiol. Anat. 25.3-4 (2003): 259-62 as Larrey's space. In other words, the distal portion of lead 18 may be implanted in the region around the outer surface of heart 26, but not attached to heart 26.

Pacing lead 18 includes an elongated lead body that contains one or more elongated electrical conductors (not illustrated) that extend within the lead body from the connector at the proximal lead end to electrodes 32 and 34 located along the distal portion of lead 18. The elongated lead body may have a generally uniform shape along the length of the lead body. In one example, the elongated lead body may have a generally tubular or cylindrical shape along the length of the lead body. The elongated lead body may have a diameter of between 3 and 9 French (Fr) in some instances. However, lead bodies of less than 3 Fr and more than 9 Fr may also be utilized. In another example, the distal portion (or all of) the elongated lead body may have a flat, ribbon or paddle shape. In this instance, the width across the flat portion of the flat, ribbon or paddle shape may be between 1 and 3.5 mm. The lead body of lead 18 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead body of lead 18 may engage with respective ones of electrodes 32 and 34. In one example, each of electrodes 32 and 34 is electrically coupled to a respective conductor within the lead body. The respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 32 and 34 and transmit sensed electrical signals from one or more of electrodes 32 and 34 to the sensing module within ICD 14.

Electrodes 32 and 34 may comprise ring electrodes, hemispherical electrodes, coil electrodes, helix electrodes, segmented electrodes, directional electrodes, or other types of electrodes, or combination thereof. Electrodes 32 and 34 may be the same type of electrodes or different types of electrodes. In the example illustrated in FIGS. 1A-C electrode 32 is a hemispherical electrode and electrode 34 is a ring or coil electrode. Electrodes 32 and 34 of lead 18 may have substantially the same outer diameter as the lead body. In one example, electrodes 32 and 34 may have surface areas between 1.6-55 mm$^2$. In another example, one or both of electrodes 32 and 34 may be coil electrodes and may have surface areas of up to 200 mm². Electrodes 32 and 34 may, in some instances, have relatively the same surface area or different surface areas. For example, electrode 32 may have a surface area of approximately 2-5 mm² and electrode 34 may have a surface area between 15-44 mm².

In some instances, electrodes 32 and 34 may be spaced apart by approximately 5-15 mm. In other instances, electrodes 32 and 34 may be spaced apart by distances greater than 15 mm. For example, electrodes 32 and 34 may be spaced apart between 2-8 cm and still both be substantially over the ventricles. In another example, electrodes 32 and 34 may be spaced apart by greater than 8 cm, e.g., up to 16 cm apart, as may be the case to obtain atrial and ventricular pacing or sensing.

The example dimensions provided above are exemplary in nature and should not be considered limiting of the embodiments described herein. In other examples, lead 18 may include a single electrode or more than two electrodes. In further examples, lead 18 may include one or more additional electrodes outside of the substernal space, e.g., near the apex of the heart or near a proximal end of lead 18.

ICD 14 may generate and deliver pacing pulses to provide anti-tachycardia pacing (ATP), bradycardia pacing, post-shock pacing, or other pacing therapies or combination of pacing therapies via pacing vectors formed using electrodes 32 and/or 34. The pacing therapy, whether it be ATP, post-shock pacing, bradycardia pacing, or other pacing therapy may be painlessly provided in an ICD system without entering the vasculature or the pericardial space, and without being attached to the heart. To the contrary, pacing therapy provided by a subcutaneous ICD system, if provided at all, is provided using pulse energies that may be uncomfortable for patient 12.

ICD 14 may deliver pacing pulses to heart 26 via a pacing vector that includes any combination of one or both of electrodes 32 and 34 and a housing electrode of ICD 14. For example, ICD 14 may deliver pacing pulses using a bipolar pacing vector between electrodes 32 and 34. In another example, ICD 14 may deliver pacing pulses using a unipolar pacing vector (e.g., between electrode 32 and the conductive housing electrode of ICD 14 or between electrode 34 and the conductive housing electrode of ICD 14). In a further example, ICD 14 may deliver pacing pulses via a pacing vector in which electrodes 32 and 34 together form the cathode (or anode) of the pacing vector and the housing electrode of ICD 14 functions as the anode (or cathode) of the pacing vector. In still further instances, ICD 14 may deliver pacing therapy via a pacing vector between electrode 32 (or electrode 34) and an electrode of defibrillation lead 16, e.g., defibrillation electrode 24 or one of electrodes 28 or 30.

ICD 14 may also obtain sensed electrical signals corresponding with electrical activity of heart 26 via one or more sensing vectors that include combinations of electrodes 32 and 34 and/or the housing electrode of ICD 14. For example, ICD 14 may obtain electrical signals sensed using a bipolar sensing vector (e.g., between electrodes 32 and 34) or via a unipolar sensing vector (e.g., between electrode 32 and the conductive housing electrode of ICD 14 or between electrode 34 and the conductive housing electrode of ICD 14), or a combination thereof. In some instances, ICD 14 may obtain sensed electrical activity of heart 26 via a sensing vector between one of electrode 32 (or electrode 34) and electrodes 24, 28 and 30 of defibrillation lead 16. ICD 14 may deliver the pacing therapy based on the electrical signals sensed via the one or more of the sensing vectors of pacing lead 18. Alternatively or additionally, ICD 14 may deliver the pacing therapy based on the electrical signals sensed via the one or more of the sensing vectors of defibrillation lead 16 or based on both the electrical signals sensed via the sensing vector(s) of pacing lead 18 and defibrillation lead 16.

Pacing lead 18 may, in alternative embodiments, include more than two electrodes or only a single electrode. In instances in which pacing lead 18 includes more than two electrodes, ICD 14 may deliver pacing pulses and/or obtain sensed electrical signals of heart 26 via any of a number of combinations of the electrodes. For example, lead 18 may be a quadripolar lead having four ring electrodes toward a distal end of lead 18 and ICD 14 may deliver pacing pulses and/or sense electrical signals via any of the combinations of electrodes or between any one of the electrodes and the housing electrode of ICD 14.

ICD 14 analyzes the sensed electrical signals obtained from one or more of the sensing vectors of pacing lead 18 and/or one or more of the sensing vectors of defibrillation lead 16 to detect tachycardia, such as ventricular tachycardia or ventricular fibrillation. ICD 14 may analyze the heart rate and/or morphology of the sensed electrical signals to monitor for tachyarrhythmia in accordance with any of a number of techniques known in the art. One example technique for detecting tachyarrhythmia is described in U.S. Pat. No. 7,761,150 to Ghanem et al., entitled "METHOD AND APPARATUS FOR DETECTING ARRHYTHMIAS IN A MEDICAL DEVICE." The entire content of the tachyarrhythmia detection algorithm described in Ghanem et al. are incorporated by reference herein in their entirety. Sensing may be completely performed via electrodes 32 and 34 of pacing lead 18 such that defibrillation lead 16 only includes a defibrillation electrode 24 and no sensing electrodes 28 or 30. In another example, ICD 14 may detect ventricular tachycardia or ventricular fibrillation using the signals sensed via electrodes 28 or 30 of defibrillation lead 16 and using the signals sensed via electrodes 32 or 34 of pacing lead 18 as a verification of the tachycardia or fibrillation.

In some instances, ICD 14 delivers one or more ATP therapies via the one or more pacing or therapy vectors of pacing lead 18 in response to detecting the tachycardia in an attempt to terminate the tachycardia without delivering a high voltage therapy, e.g., defibrillation shock or cardioversion shock. If the one or more ATP therapies are not successful or it is determined that ATP therapy is not desired, ICD 14 may deliver one or more cardioversion or defibrillation shocks via defibrillation electrode 24 of defibrillation lead 16. In other examples, ICD 14 may be configured to provide pacing therapy via a combination of therapy vectors that include combinations of electrodes 28 and/or 30 and the housing electrode of ICD 14 or via a therapy vector that includes one of electrodes 28 or 30 (or defibrillation electrode 24) and one of electrodes 32 or 34 of pacing lead 18. For example, ICD 14 may provide ATP and post-shock pacing using at least one electrode of defibrillation lead 16. In this case, lead 18 may be only utilized for sensing. In another example, ICD 14 may provide ATP using a therapy vector using an electrode of pacing lead 18 and deliver post-shock therapy using a therapy vector including an electrode of lead 16.

The configuration described above in FIGS. 1A-1C is directed to providing ventricular therapies via defibrillation lead 16 and pacing lead 18. In some instances, it may be desirable to provide atrial therapy in addition to or instead of ventricular therapy. In situations in which atrial pacing or sensing is desired in addition to or instead of ventricular pacing, pacing lead 18 may be positioned further superior. A pacing lead configured to deliver pacing pulses to both the atrium and ventricle may have more electrodes. For example, the pacing lead may have one or more electrodes located over a cardiac silhouette of the atrium as observed via the AP fluoroscopic view of heart 26 and one or more electrodes located over a cardiac silhouette of the ventricle as observed via the AP fluoroscopic view of heart 26. A pacing lead configured to deliver pacing pulses to only the atrium may, for example, have one or more electrodes located over a cardiac silhouette of the atrium as observed via the AP fluoroscopic view of heart 26. In some instances, two substernal pacing leads may be utilized with one being an atrial pacing lead implanted such that the electrodes are located over a cardiac silhouette of the atrium as observed via the AP fluoroscopic view of heart 26 and the other being a ventricle pacing lead being implanted such that the electrodes are located over a cardiac silhouette of the ventricle as observed via the AP fluoroscopic view of heart 26.

Likewise, it may be desirable to provide atrial therapies using defibrillation lead 16. In such a case, defibrillation lead 16 may include more than one defibrillation electrode and be placed further superior along sternum 22 such that a first therapy vector exists for the ventricle (e.g., via defibrillation electrode 24) and a second therapy vector exists for the atrium (e.g., via a second defibrillation electrode). In another example, defibrillation lead 16 may be placed further superior along sternum 22 such that a therapy vector between defibrillation electrode 24 and a housing electrode of ICD 14 is substantially across an atrium of heart 26, such that extravascular ICD system 10 may be used to provide atrial therapies to treat atrial fibrillation.

ICD 14 may include a housing that forms a hermetic seal that protects components of ICD 14. The housing of ICD 14 may be formed of a conductive material, such as titanium. ICD 14 may also include a connector assembly (also referred to as a connector block or header) that includes electrical feedthroughs through which electrical connections are made between conductors within leads 16 and 18 and electronic components included within the housing. As will be described in further detail herein, housing may house one or more processors, memories, transmitters, receivers, sensors, sensing circuitry, therapy circuitry, power sources and other appropriate components. The housing is configured to be implanted in a patient, such as patient 12.

Like lead 18, lead 16 includes a lead body that contain one or more elongated electrical conductors (not illustrated) that extend through the lead body from the connector at a proximal lead end to the electrodes 24, 28, and 30. The lead bodies of leads 16 and 18 may be formed from a non-conductive material, including silicone, polyurethane, fluoropolymers, mixtures thereof, and other appropriate materials, and shaped to form one or more lumens within which the one or more conductors extend. The respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 24, 28, and 30 and transmit sensed electrical signals from one or more of electrodes 24, 28, and 30 to the sensing module within ICD 14. However, the techniques are not limited to such constructions.

The leads 16 and 18 may further include one or more anchoring mechanisms that are positioned along the length of the lead body. The anchoring mechanisms affix the lead 18 that is implanted in a substernal space in a fixed location to prevent dislodging of the lead 18 once it is implanted. For example, the lead 18 may be anchored at one or more locations situated between the distal lead end positioned within the substernal space of patient 12 and a point along the length of the portion of the lead body at or near the insertion point of the lead body into the substernal space. The one or more anchoring mechanism(s) may either engage bone, fascia, muscle or other tissue of patient 12 or may simply be wedged therein to affix the lead under the sternum to prevent excessive motion or dislogment. Furthermore, it should be understood that various anchoring mechanisms described in this disclosure may additionally be utilized for delivery of a stimulation therapy as is known in the art.

In accordance with various embodiments of the invention, this disclosure describes anchoring mechanisms that are integrated into the lead body. In such embodiments, a portion or segment of the lead body may be formed with materials that function to encase conductors and other elements internal to the lead while also anchoring the lead within the implant environment.

In alternative embodiments, anchoring mechanisms of the disclosure are described as discrete elements that may be formed in line with the lead body. In some embodiments, the discrete components may be provided in a fixedly-secured relationship to the lead body. In other embodiments, the anchoring mechanism may be detachedly coupled in a sliding relationship over the lead body.

The anchoring mechanisms may include a passive anchoring mechanism, an active anchoring mechanism or a combination of both. In one embodiment, the anchoring mechanism is coupled at a distal end of the lead body and may also function as an electrically active element. Examples of passive anchoring mechanisms include flanges, disks, pliant tines, flaps, porous structures such as a mesh-like element that facilitate tissue growth for engagement, bio-adhesive surfaces, and/or any other non-piercing elements. Examples of active anchoring mechanisms may include rigid tines, prongs, barbs, clips, screws, and/or other projecting elements that pierce and penetrate into tissue to anchor the lead. As another example of an active anchoring mechanism, the lead may be provided with a side helix for engaging tissue.

The various examples of the anchoring mechanisms may be deployable. As such, the anchoring mechanism assumes a first state during maneuvering of the lead (during which time the lead is disposed within a lumen of a delivery system or overtop a guidewire or stylet) to the desired implant location. Subsequently, the anchoring mechanism assumes a second state following the release of the lead from the delivery system into the substernal space to thereby anchor the distal end portion of the lead body relative to the adjacent tissue.

In addition or alternatively, the lead may be anchored through a suture that fixedly-secures the lead to the patient's musculature, tissue or bone at the xiphoid entry site. In some embodiments, the suture may be sewn through pre-formed suture holes to the patient.

The examples illustrated in FIGS. 1A-C are exemplary in nature and should not be considered limiting of the techniques described in this disclosure. In other examples, ICD 14, defibrillation lead 16, and pacing lead 18 may be implanted at other locations. For example, ICD 14 may be implanted in a subcutaneous pocket in the right pectoral region. In this example, defibrillation lead 16 may extend subcutaneously from the device toward the manubrium of the sternum and bend or turn and extend subcutaneously inferiorly from the manubrium of the sternum, substantially parallel with the sternum and pacing lead 18 may extend subcutaneously from the device toward the manubrium of the sternum to the desired location and bend or turn and extend inferior from the manubrium underneath/below sternum 22 to the desired location. In yet another example, implantable pulse generator 14 may be placed abdominally.

In the example illustrated in FIG. 1, system 10 is an ICD system that provides cardioversion/defibrillation and pacing therapy. However, these techniques may be applicable to other cardiac systems, including cardiac resynchronization therapy defibrillator (CRT-D) systems or other cardiac stimulation therapies, or combinations thereof. For example, ICD 14 may be configured to provide electrical stimulation pulses to stimulate nerves, skeletal muscles, diaphragmatic muscles, e.g., for various neuro-cardiac applications and/or for apnea or respiration therapy. In addition, it should be noted that system 10 may not be limited to treatment of a human patient. In alternative examples, system 10 may be implemented in non-human patients, e.g., primates, canines, equines, pigs, ovines, bovines, and felines. These other animals may undergo clinical or research therapies that may benefit from the subject matter of this disclosure.

Figure 2:
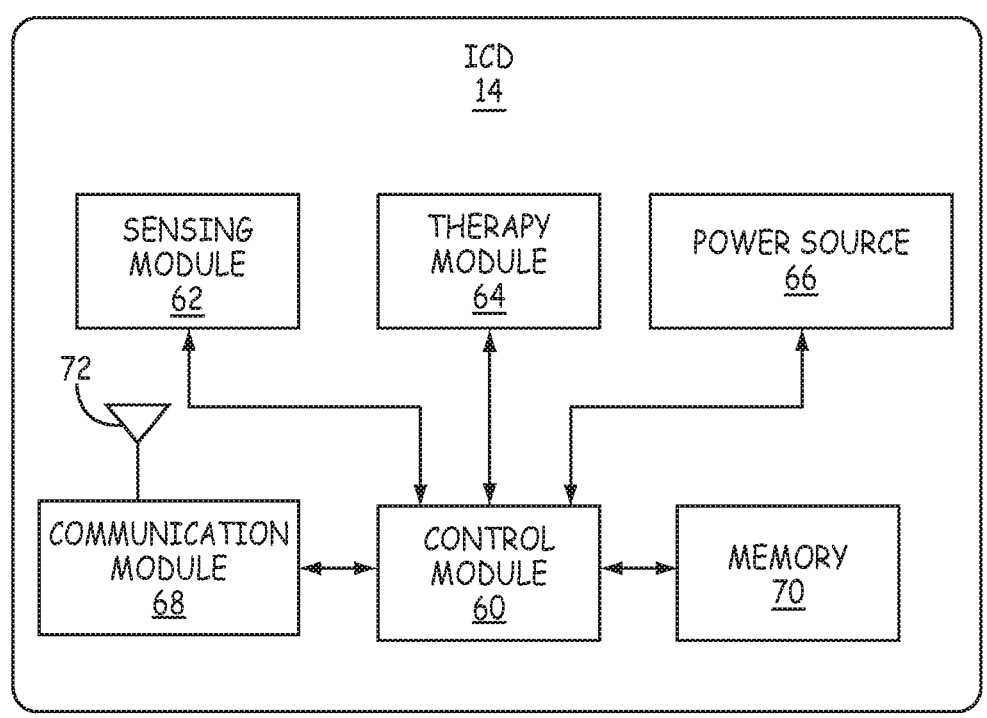
FIG. 2 is a functional block diagram of an example configuration of electronic components of an example implantable cardioverter-defibrillator (ICD).

FIG. 2 is a functional block diagram of an example configuration of electronic components of an example ICD 14. ICD 14 includes a control module 60, sensing module 62, therapy module 64, communication module 68, and memory 70. The electronic components may receive power from a power source 66, which may, for example, be a rechargeable or non-rechargeable battery. In other embodiments, ICD 14 may include more or fewer electronic components. The described modules may be implemented together on a common hardware component or separately as discrete but interoperable hardware, firmware or software components. Depiction of different features as modules is intended to highlight different functional aspects and does not necessarily imply that such modules must be realized by separate hardware, firmware or software components. Rather, functionality associated with one or more modules may be performed by separate hardware, firmware or software components, or integrated within common or separate hardware, firmware or software components.

Sensing module 62 is electrically coupled to some or all of electrodes 24, 28, 30, 32, and 34 via the conductors of leads 16 and 18 and one or more electrical feedthroughs, and is also electrically coupled to the housing electrode via conductors internal to the housing of ICD 14. Sensing module 62 is configured to obtain signals sensed via one or more combinations of electrodes 24, 28, 30, 32, 34, and the housing electrode of ICD 14 and process the obtained signals.

The components of sensing module 62 may be analog components, digital components or a combination thereof. Sensing module 62 may, for example, include one or more sense amplifiers, filters, rectifiers, threshold detectors, analog-to-digital converters (ADCs) or the like. Sensing module 62 may convert the sensed signals to digital form and provide the digital signals to control module 60 for processing or analysis. For example, sensing module 62 may amplify signals from the sensing electrodes and convert the amplified signals to multi-bit digital signals by an ADC. Sensing module 62 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to control module 60.

Control module 60 may process the signals from sensing module 62 to monitor electrical activity of heart 26 of patient 12. Control module 60 may store signals obtained by sensing module 62 as well as any generated EGM waveforms, marker channel data or other data derived based on the sensed signals in memory 70. Control module 60 also analyzes the EGM waveforms and/or marker channel data to detect cardiac events (e.g., tachycardia). In response to detecting the cardiac event, control module 60 may control therapy module 64 to generate and deliver the desired therapy according to one or more therapy programs, which may be stored in memory 70, to treat the cardiac event. The therapy may include, but is not limited to, defibrillation or cardioversion shock(s), ATP, post-shock pacing, bradycardia pacing, or the like.

Therapy module 64 is configured to generate and deliver electrical stimulation therapy to heart 26. Therapy module 64 may include one or more pulse generators, capacitors, and/or other components capable of generating and/or storing energy to deliver as pacing therapy, defibrillation therapy, cardioversion therapy, cardiac resynchronization therapy, other therapy or a combination of therapies. In some instances, therapy module 64 may include a first set of components configured to provide pacing therapy and a second set of components configured to provide defibrillation therapy. In other instances, the same set of components may be configurable to provide both pacing and defibrillation therapy. In still other instances, some of the defibrillation and pacing therapy components may be shared components while others are used solely for defibrillation or pacing.

Therapy module 64 delivers the generated therapy to heart 26 via one or more combinations of electrodes 24, 28, 30, 32, 34, and the housing electrode of ICD 14. Control module 60 controls therapy module 64 to generate electrical stimulation therapy with the amplitudes, pulse widths, timing, frequencies, or electrode combinations specified by the selected therapy program.

In the case of pacing therapy, e.g., ATP, post-shock pacing, and/or bradycardia pacing provided via electrodes 32 and/or 34 of pacing lead 18, control module 60 controls therapy module 64 to generate and deliver pacing pulses with any of a number of amplitudes and pulse widths to capture heart 26. The pacing thresholds of heart 26 when delivering pacing pulses from the anterior mediastinum using pacing lead 18 may depend upon a number of factors, including location, type, size, orientation, and/or spacing of electrodes 32 and 34, location of ICD 14 relative to electrodes 32 and 34, physical abnormalities of heart 26 (e.g., pericardial adhesions or myocardial infarctions), or other factor(s).

The increased distance from electrodes 32 and 34 of pacing lead 18 to the heart tissue may result in heart 26 having increased pacing thresholds compared to transvenous pacing thresholds. To this end, therapy module 64 may be configured to generate and deliver pacing pulses having larger amplitudes and/or pulse widths than conventionally required to obtain capture via transvenously implanted lead or a lead attached to heart 26. In one example, therapy module 64 may generate and deliver pacing pulses having amplitudes of less than or equal to 8 volts and pulse widths between 0.5-3.0 milliseconds. In another example, therapy module 64 may generate and deliver pacing pluses having amplitudes of between 5 and 10 volts and pulse widths between approximately 3.0 milliseconds and 10.0 milliseconds. In another example, therapy module 64 may generate and deliver pacing pluses having pulse widths between approximately 2.0 milliseconds and 8.0 milliseconds. In a further example, therapy module 64 may generate and deliver pacing pluses having pulse widths between approximately 0.5 milliseconds and 20.0 milliseconds. In another example, therapy module 64 may generate and deliver pacing pluses having pulse widths between approximately 1.5 milliseconds and 20.0 milliseconds.

In some cases, therapy module 64 may generate pacing pulses having longer pulse durations than conventional transvenous pacing pulses to achieve lower energy consumption. For example, therapy module 64 may be configured to generate and deliver pacing pulses having pulse widths or durations of greater than two (2) milliseconds. In another example, therapy module 64 may be configured to generate and deliver pacing pulses having pulse widths or durations of between greater than two (2) milliseconds and less than or equal to three (3) milliseconds. In another example, therapy module 64 may be configured to generate and deliver pacing pulses having pulse widths or durations of greater than or equal to three (3) milliseconds. In another example, therapy module 64 may be configured to generate and deliver pacing pulses having pulse widths or durations of greater than or equal to five (5) milliseconds. In another example, therapy module 64 may be configured to generate and deliver pacing pulses having pulse widths or durations of greater than or equal to ten (10) milliseconds. In a further example, therapy module 64 may be configured to generate and deliver pacing pulses having pulse widths between approximately 3-10 milliseconds. In a further example, therapy module 64 may be configured to generate and deliver pacing pulses having pulse widths or durations of greater than or equal to fifteen (15) milliseconds. In yet another example, therapy module 64 may be configured to generate and deliver pacing pulses having pulse widths or durations of greater than or equal to twenty (20) milliseconds.

Depending on the pulse widths, ICD 14 may be configured to deliver pacing pulses having pulse amplitudes less than or equal to twenty (20) volts, deliver pacing pulses having pulse amplitudes less than or equal to ten (10) volts, deliver pacing pulses having pulse amplitudes less than or equal to five (5) volts, deliver pacing pulses having pulse amplitudes less than or equal to two and one-half (2.5) volts, deliver pacing pulses having pulse amplitudes less than or equal to one (1) volt. In other examples, the pacing pulse amplitudes may be greater than 20 volts. Typically the lower amplitudes require longer pacing widths as illustrated in the experimental results. Reducing the amplitude of pacing pulses delivered by ICD 14 reduces the likelihood of extra-cardiac stimulation. Some experimental results are provided later illustrating some example combinations of pacing amplitudes and widths.

In the case of defibrillation therapy, e.g., defibrillation or cardioversion shocks provided by defibrillation electrode 24 of defibrillation lead 16, control module 60 controls therapy module 64 to generate defibrillation or cardioversion shocks having any of a number of waveform properties, including leading-edge voltage, tilt, delivered energy, pulse phases, and the like. Therapy module 64 may, for instance, generate monophasic, biphasic or multiphasic waveforms. Additionally, therapy module 64 may generate defibrillation waveforms having different amounts of energy. For example, therapy module 64 may generate defibrillation waveforms that deliver a total of between approximately 60-80 Joules (J) of energy. Therapy module 64 may also generate defibrillation waveforms having different tilts. In the case of a biphasic defibrillation waveform, therapy module 64 may use a 65/65 tilt, a 50/50 tilt, or other combinations of tilt. The tilts on each phase of the biphasic or multiphasic waveforms may be the same in some instances, e.g., 65/65 tilt. However, in other instances, the tilts on each phase of the biphasic or multiphasic waveforms may be different, e.g., 65 tilt on the first phase and 55 tilt on the second phase. The example delivered energies, leading-edge voltages, phases, tilts, and the like are provided for example purposes only and should not be considered as limiting of the types of waveform properties that may be utilized to provide subcutaneous defibrillation via defibrillation electrode 24.

Communication module 68 includes any suitable hardware, firmware, software or any combination thereof for communicating with another device, such as a clinician programmer, a patient monitoring device, or the like. For example, communication module 68 may include appropriate modulation, demodulation, frequency conversion, filtering, and amplifier components for transmission and reception of data with the aid of antenna 72. Antenna 72 may be located within the connector block of ICD 14 or within housing ICD 14.

The various modules of ICD 14 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 70 may include computer-readable instructions that, when executed by control module 60 or other component of ICD 14, cause one or more components of ICD 14 to perform various functions attributed to those components in this disclosure. Memory 70 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Figure 3:
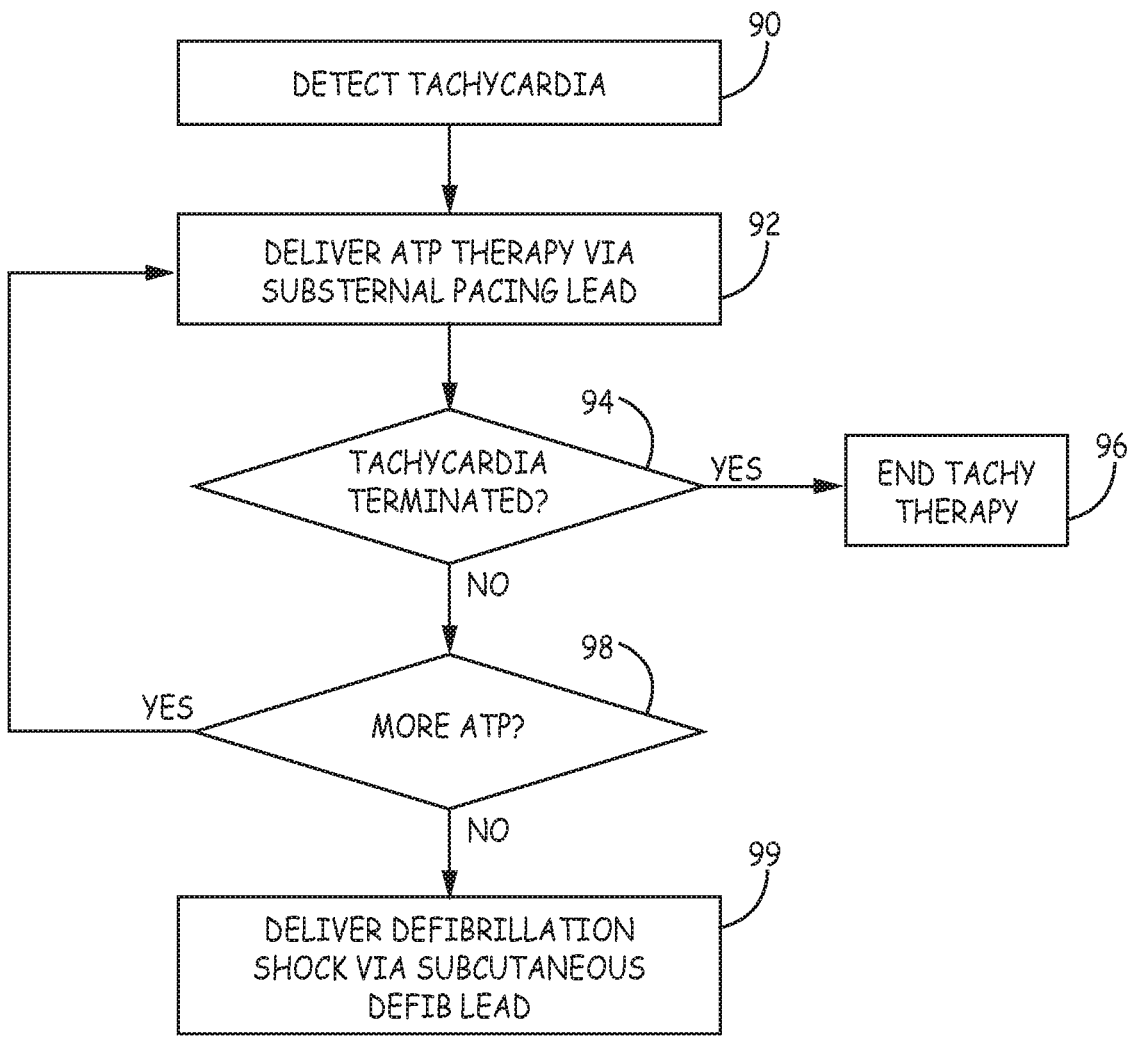
FIG. 3 is a flow diagram illustrating example operation of an implantable cardiac system having a substernal pacing lead.

FIG. 3 is a flow diagram illustrating example operation of an implantable cardiac system, such as implantable cardiac system 10 of FIGS. 1A-1C. Initially, ICD 14 analyzes sensed electrical signals from one or more sensing vectors of pacing lead 18 and/or one or more sensing vectors of defibrillation lead 16 to detect tachycardia, such as ventricular tachycardia or ventricular fibrillation (90).

ICD 14 deliver a sequence of ATP pacing pulses via a therapy vector that includes at least one electrode of pacing lead 18, which is implanted in the substernal space (92). ICD 14 may deliver the sequence of ATP pacing pulses to heart 26 via a pacing vector that includes any combination of one or both of electrodes 32 and 34 and a housing electrode of ICD 14, e.g., via a bipolar or unipolar pacing vector. Alternatively, ICD 14 may deliver the sequence of ATP pacing pulses via a therapy vector between one of the electrodes of pacing lead 18 and an electrode of defibrillation lead 16. As described above, the pacing pulses provided by ICD 14 may have longer pulse widths than conventional pacing pulses. For example, ICD 14 may be configured to deliver pacing pulses having pulse widths of greater than two milliseconds. In other instances, ICD 14 may be configured to deliver pacing pulses having pulse widths of between three and ten milliseconds. Other ranges of pulse widths, as well as pacing amplitudes, rates, number of pulses, and the like and various combinations of characteristics are described in further detail herein.

In some instances, ICD 14 may be configured to only deliver ATP to particular types of tachyarrhythmias. ICD 14 may, for example, distinguish between VT and VF and only provide ATP in instances in which the tachycardia is VT. If the tachycardia is VF, the ICD 14 may be configured to not provide ATP and instead only deliver defibrillation therapy.

After delivery of the sequence of ATP pacing pulses, ICD 14 determines whether the tachycardia is terminated (94). ICD 14 may, for example, analyze the most recent sensed activity of the heart to determine if the sequence of ATP pacing pulses terminated the tachycardia. When ICD 14 determines that the tachycardia has terminated ("YES" branch of block 94), ICD 14 ends the tachycardia therapy and returns to analyzing sensed electrical signals (96).

When ICD 14 determines that the tachycardia has not terminated ("NO" branch of block 94), ICD 14 determines whether additional sequences of ATP pacing pulses will be provided (98). ICD 14 may, for example, be configured to deliver ATP therapy that consists of two or more sequences of ATP pacing pulses. When ICD 14 determines that additional sequences of ATP pacing pulses will be provided ("YES" branch of block 98), ICD 14 delivers a second sequence of ATP pacing pulses via a therapy vector that includes at least one electrode of pacing lead 18, which is implanted in the substernal space (92). The second sequence of pacing pulses may be the same as the first sequence. Alternatively, the second sequence of pacing pulses may be different than the first sequence. For example, the ATP pulses of the first and second sequences of pulses may have one or more different characteristics including, but not limited to, different pacing amplitudes, pulse widths, rates, therapy vectors, and/or variation among pacing pulses.

When ICD 14 determines that no additional sequences of ATP pacing pulses will be provided ("NO" branch of block 98), ICD 14 delivers a defibrillation pulse via a therapy vector that includes defibrillation electrode 24 of defibrillation lead 16 (99). As described with respect to FIGS. 1A-1C, defibrillation lead 16 may, in some instances, be implanted subcutaneously between the skin and the sternum and/or ribcage. Alternatively, defibrillation lead 16 may be implanted at least partially in the substernal space or other extravascular location, as described with respect to FIGS. 10A and 10B. The amount of energy of the defibrillation pulse will depend on the location of the defibrillation electrode 24 as described in further detail herein.

EXPERIMENTS

Three acute procedures were performed using pigs, with the animals in a dorsal recumbency. An incision was made near the xiphoid process and a Model 4194 lead was delivered to the substernal/retrosternal space using a 6996T tunneling tool and sheath. An active can emulator (ACE) was placed in a subcutaneous pocket on either the right chest (first acute experiment) or the left midaxillary (second and third acute experiments). Various pacing configurations were tried and different pieces of equipment were used as the source of stimulation. Multiple pulse widths were used in delivering the pacing pulse. Across experiments, several different substernal/retrosternal lead electrode locations were utilized.

In the second and third experiments the impact of lead location on electrical performance was investigated by moving the lead to several locations under the sternum and collecting data to generate strength-duration curves at each location.

In all three acute experiments, the substernal/retrosternal lead was placed and electrical data collected. The lead was moved intentionally many times across experiments to better understand the location best suited to capturing the heart at low pacing thresholds, with different locations and parameters tried until pacing capability was gained and lost. A range of thresholds based on location and pacing configuration was recorded. For this reason, the lowest threshold result for each acute experiment is reported, as are strength-duration curves showing the range of pacing values obtained from suitable pacing locations. In all cases, it was determined that positioning the substernal/retrosternal pacing electrode approximately over the ventricle of the cardiac silhouette provided best results.

Experiment 1

In the first acute study, a Medtronic Attain bipolar OTW 4194 lead was implanted substernally/retrosternally, and two active can emulators were positioned, one in the right dorsal lateral region (ACE1) and one on the right midaxillary (ACE2). The 4194 lead was placed directly below the sternum, in the mediastinum, with the lead tip and body running parallel to the length of the sternum. Various pacing configurations were tried and electrical data collected.

The smallest threshold observed was 0.8 volts, obtained when pacing from the tip of the substernal/retrosternal 4194 lead to ACE1 (10 ms pulse width and Frederick Heir instrument as the source of stimulation). It was possible to capture using a smaller pulse width, though threshold increased as the pulse width shortened (1.5V at 2 ms in this same configuration with a bp isolater, made by FHC product #74-65-7, referred to herein as "Frederick Heir Stimulator." Many additional low thresholds (1-2 volts) were obtained with different pacing configurations and pulse durations.

Figure 4:
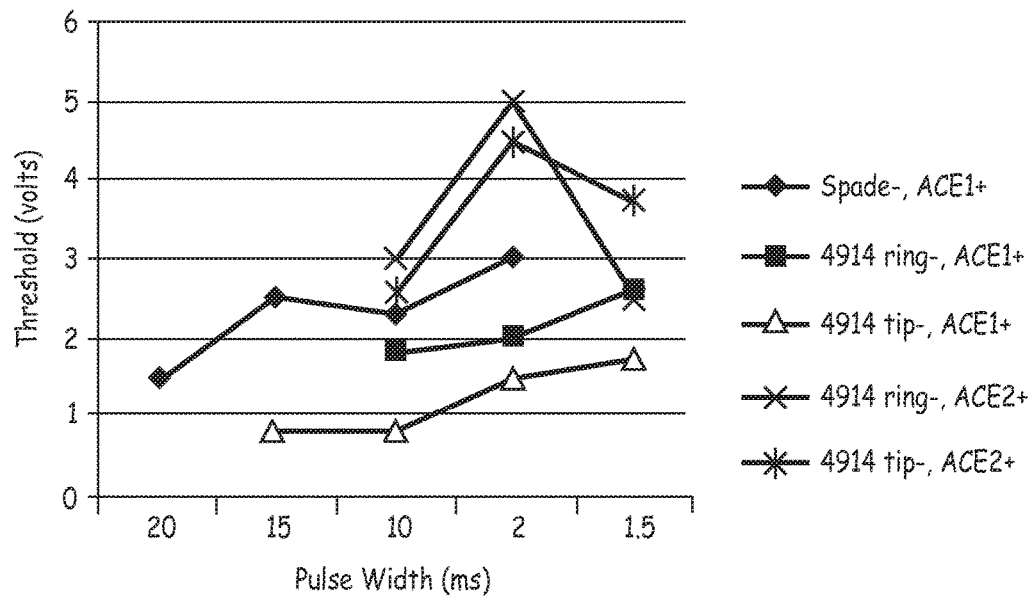
FIG. 4 is a graph illustrating strength-duration curves showing the capture thresholds obtained at various pulse widths during a first acute study.

FIG. 4 illustrates a strength-duration curve showing the capture thresholds obtained at various pulse widths during the first acute study. Note that all configurations paced from either the tip or the ring of the substernally/retrosternally implanted 4194 lead (−) to one of the two active can emulators (+). In one instance, a large spade electrode (instead of a Model 4194 lead) was used as the substernal/retrosternal electrode, as noted in the legend of FIG. 4.

As shown, several pacing configurations and parameters were tried. Across the configurations reported in the graph above, threshold values ranged from 0.8 volts to 5.0 volts, with threshold generally increasing as pulse width was shortened. In a few instances, the threshold at 1.5 ms pulse width was smaller than the threshold at 2.0 ms. It should be noted that the threshold value obtained at 1.5 ms was always recorded using the Medtronic 2290 analyzer as the stimulation source, whereas all other threshold measurements for the first acute experiment (at pulse widths of 2, 10, 15 and 20 ms) were obtained using a Frederick Heir instrument as the source of stimulation. Differences in these two instruments may account for the difference in threshold values at similar pulse widths (1.5 ms and 2 ms).

In general, the first acute experiment demonstrated the feasibility of substernal/retrosternal pacing by producing small capture thresholds (average=2.5±1.2 volts), using several different pacing configurations and parameters.

Experiment 2

A second acute experiment was conducted. In the second acute, however, the animal presented with pericardial adhesions to the sternum. Because of the pericardial adhesion, the ventricular surface of the cardiac silhouette was rotated away from the sternum—an anatomical difference that may have resulted in higher thresholds throughout this experiment.

As in the previous acute experiment, a Model 4194 lead was placed under the sternum. An active can emulator was placed on the left midaxillary. The tip to ring section of the 4194 was positioned over the cardiac silhouette of the ventricle, as observed by fluoroscopy, and this position is notated "Position A" on the strength-duration graph illustrated in FIG. 5. The lead eventually migrated a very short distance closer to the xiphoid process during stimulation (still under the sternum) to reach "Position B," and additional electrical measurements were obtained successfully from this position as well.

The smallest threshold observed in the second acute experiment was 7V, obtained when pacing from the substernal/retrosternal 4194 ring electrode (−) to an ACE (+) on the left midaxillary in the first lead position (5 ms, 15 ms and 20 ms pulse widths, Frederick Heir stimulator). Additionally, thresholds of 8 and 9 volts were obtained with the lead in the second anatomical position, both from 4194 tip to ACE (unipolar) and 4194 tip to ring (bipolar) configurations at multiple pulse widths. The two lines that appear to run off the chart were instances of no capture.

Figure 5:
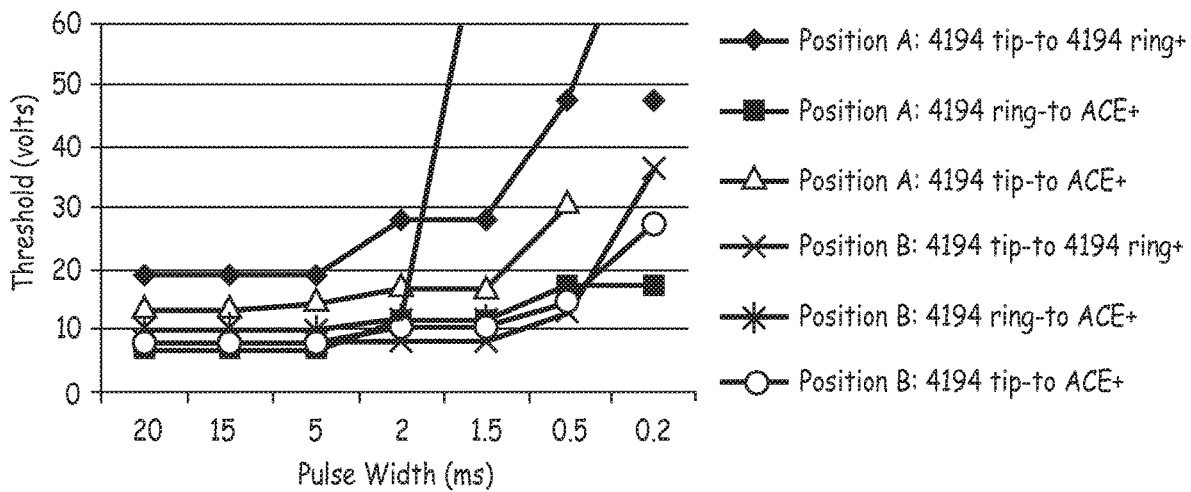
FIG. 5 is a graph illustrating strength-duration curves showing the capture thresholds obtained at various pulse widths during a second acute study.

All of the electrical values reported in FIG. 5 were collected with the Frederick Heir instrument as the stimulation source. Extra-cardiac stimulation was observed with many of the electrical measurements obtained in a unipolar pacing configuration. No obvious extra-cardiac stimulation was observed when pacing in a bipolar configuration (4194 tip to ring), though a low level of stimulation could be felt with a hand on the animal's chest.

Experiment 3

A third and final acute experiment was conducted demonstrating the feasibility of substernal/retrosternal pacing. As in the previous two acute experiments, a 4194 lead was placed under the sternum. An active can emulator was placed on the left midaxillary. In this experiment, the substernal/retrosternal 4194 lead was intentionally positioned so that the lead tip was initially near the second rib, far above the cardiac silhouette of the ventricle. The lead tip was then pulled back (toward the xiphoid process) one rib space at a time, collecting electrical data at each position. As in previous experiments, low capture thresholds were obtained when the pacing electrodes were approximately positioned over the ventricular surface of the cardiac silhouette, as observed via fluoroscopy. When the lead tip was not over the ventricular surface of the cardiac silhouette, "no capture" was often the result.

As in previous experiments, pacing was performed from either the tip or the ring of the substernal/retrosternal 4194 lead (−) to the ACE (+) on the left midaxillary. However, in this acute experiment, a subcutaneous ICD lead was also positioned in its subcutaneous arrangement (as illustrated and described in FIGS. 1A-C). In some instances, the pacing configuration was from either the tip or the ring of the substernal/retrosternal 4194 lead (−) to either the ring or the coil of the subcutaneous ICD lead (+), so that the ICD lead and not the ACE was the indifferent electrode.

The smallest threshold observed across the experiment was 0.8V, obtained when pacing from the substernal/retrosternal 4194 tip electrode (−) to an ACE (+) on the left midaxillary when the lead was positioned such that the lead tip electrode was approximately under the sixth rib (20 ms pulse width and Frederick Heir stimulator). Many additional low thresholds were obtained with different pacing configurations, shorter pulse durations and different lead positions, again demonstrating the feasibility of substernal/retrosternal pacing. Obvious extra-cardiac stimulation generally was not observed with lower threshold measurements (at longer pulse durations) but was observed at higher thresholds.

Figure 7:
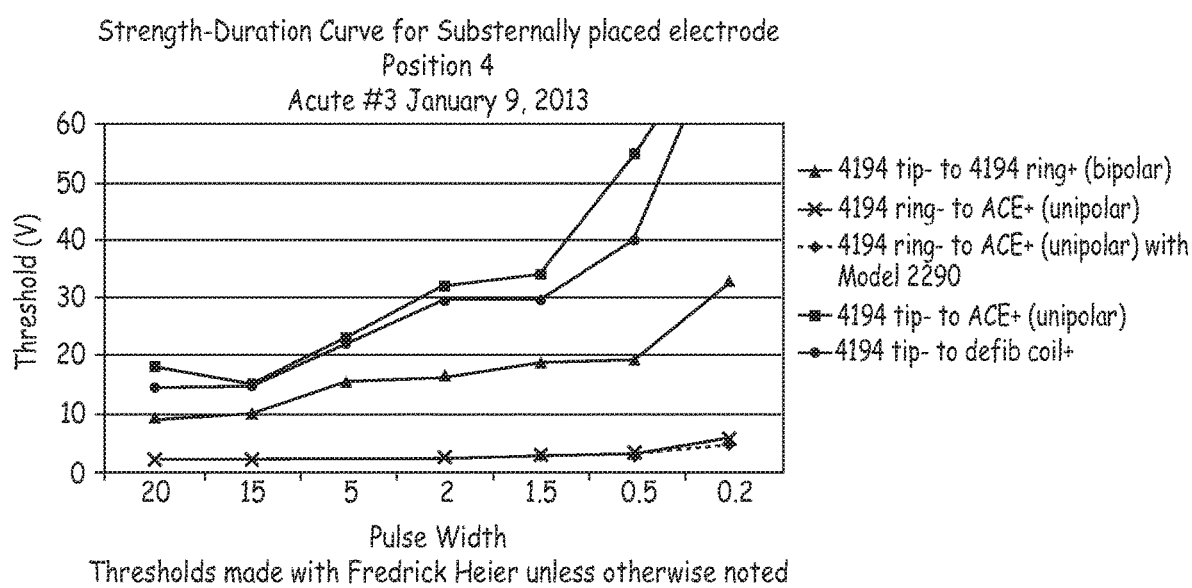
FIG. 7 is a graph illustrating strength-duration curves of electrical data from the third acute experiment with the lead positioned under the sternum in a second location.
Figure 8:
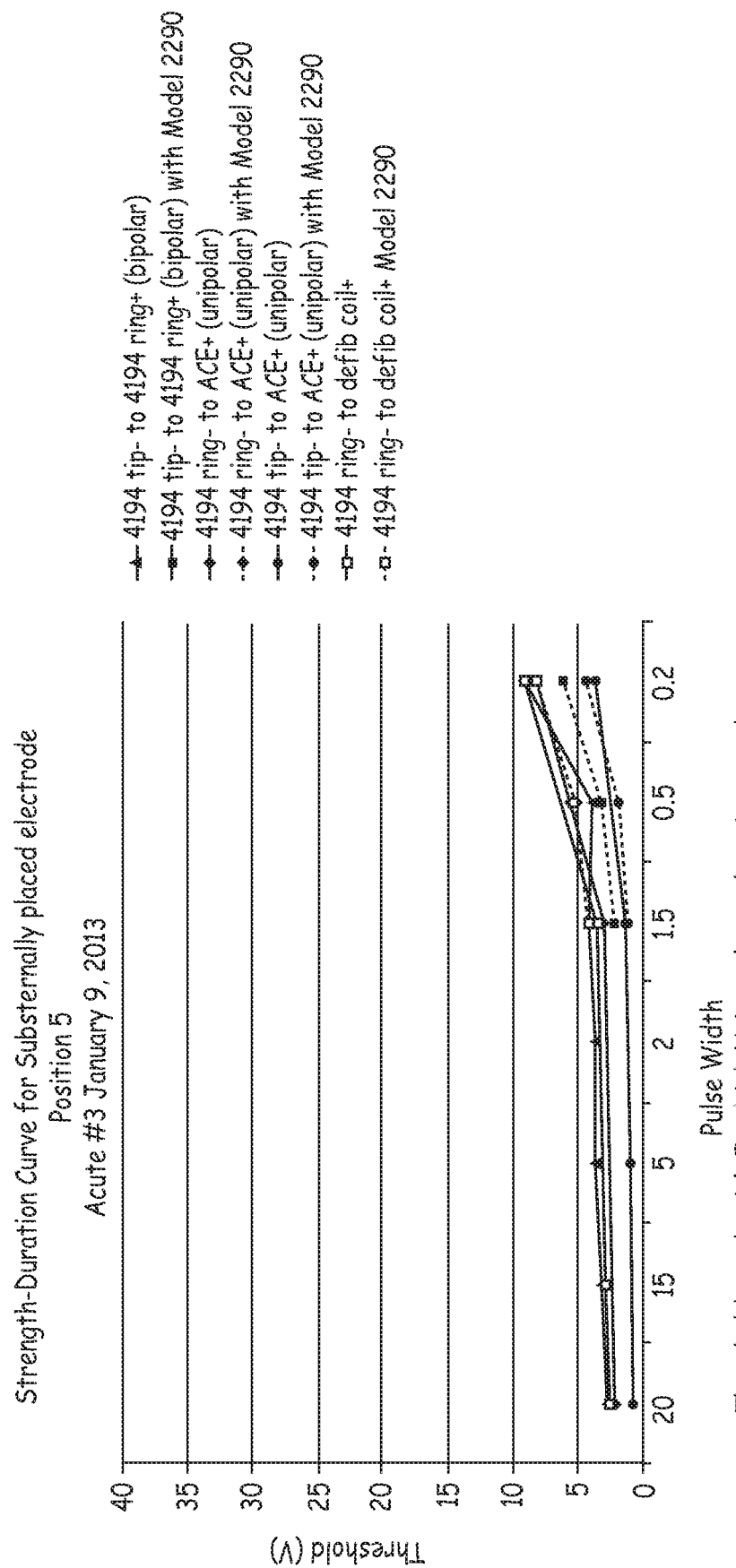
FIG. 8 is a graph illustrating strength-duration curves of electrical data from a third acute experiment with the lead positioned under the sternum in a third location.
Figure 9:
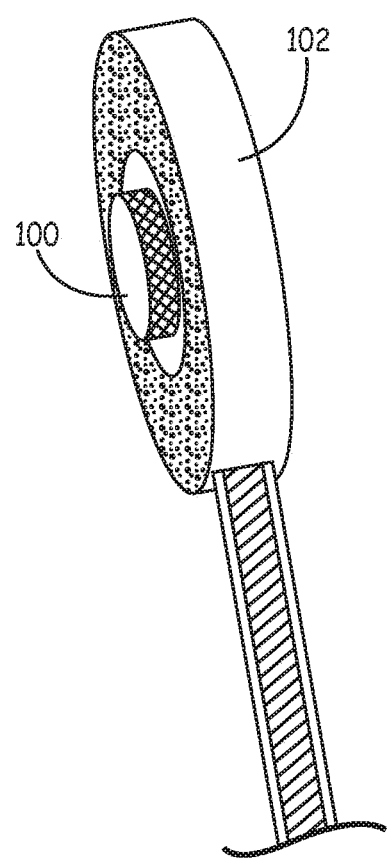
FIG. 9 is a schematic diagram illustrating an example electrode of a pacing lead to be implanted in the substernal space.

The strength duration curves for lead positions 3-5 are presented in FIGS. 7-9, with individual graphs for each location due to the breadth of electrical data collected. Measurements made with the 2290 analyzer as the source of stimulation are noted. Other electrical measurements were made with the Frederick Heir instrument as the stimulation source.

Figure 6:
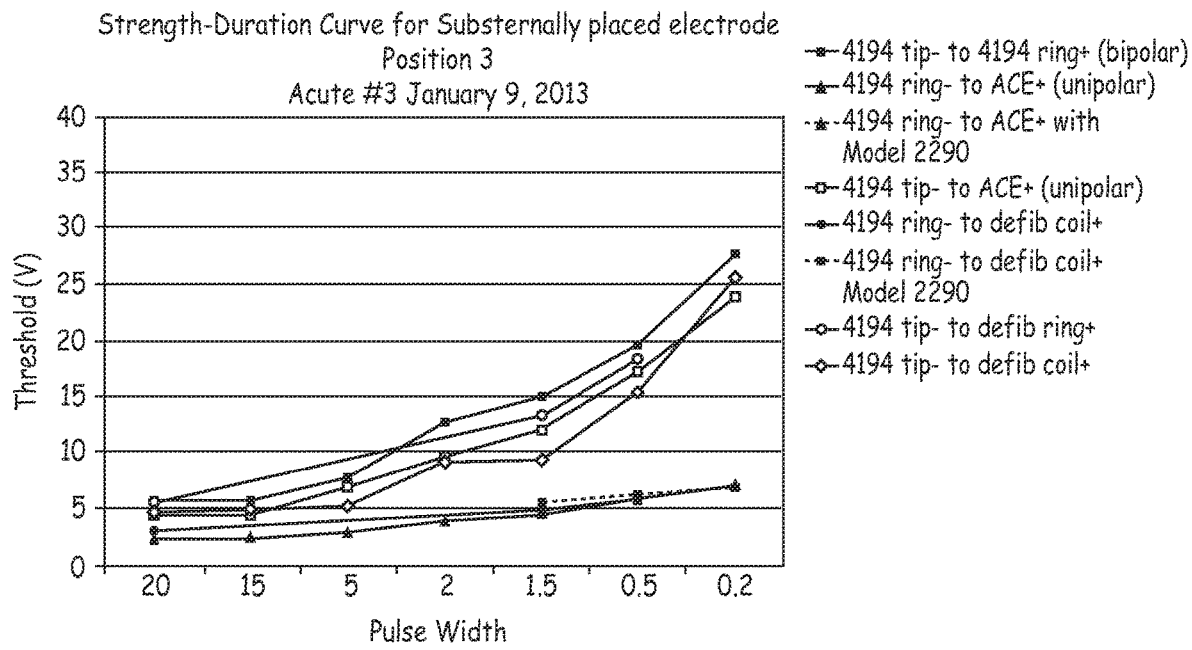
FIG. 6 is a graph illustrating strength-duration curves of electrical data from a third acute experiment with the lead positioned under the sternum in a first location.

FIG. 6 illustrates the strength-duration curve of electrical data from the third acute experiment when the 4194 lead tip was positioned under the sternum near the location of the $4^{th}$ rib. Several therapy vectors resulted in low pacing thresholds, generally when pulse widths were quite long. At shorter pulse widths, threshold increased.

FIG. 7 illustrates the strength-duration curve of electrical data from the third acute experiment when the 4194 lead tip was positioned under the sternum near the location of the $5^{th}$ rib. The two lines that appear to run off the chart at 0.2 ms were instances of no capture. FIG. 7 demonstrates the position dependence of the substernal/retrosternal lead. Thresholds were higher overall in this anatomical location (the lead tip near the $5^{th}$ rib), though capture was still possible and in the 4194 ring (−) to ACE (+) configuration, moderately low (2 volts at 20 ms). There generally was no significant extra-cardiac stimulation observed except with pulse widths of 0.2 ms and 0.5 ms in the 4194 tip (−) to ACE (+) configuration and in the unipolar configuration going from the 4194 tip (−) to the coil of the subcutaneous ICD lead at pulse widths of 1.5 ms and shorter, all of which resulted in the highest recorded threshold readings in this lead position.

FIG. 8 illustrates the strength-duration curve of electrical data from the third acute experiment when the 4194 lead tip was positioned under the sternum near the location of the $6^{th}$ rib. FIG. 8 shows the position dependence of the substernal/retrosternal electrode. When the pacing electrode is optimally located over the ventricular surface of the cardiac silhouette (as observed via fluoroscopy), pacing threshold is low. Low thresholds were very repeatable in this anatomical location, even at shorter pulse durations and in many different pacing configurations. Extra-cardiac stimulation generally was not apparent at low thresholds and longer pulse durations throughout this experiment.

All three acute experiments demonstrated the feasibility of pacing from a sub sternal/retrosternal electrode location. The lowest threshold results across the three acute procedures were 0.8 volts, 7 volts and 0.8 volts, respectively, with the second acute procedure involving an anatomical difference (pericardial adhesions) that tipped the ventricular surface of the heart away from its normal orientation with the sternum, resulting in higher pacing thresholds. However, for the purposes of anti-tachycardia pacing, conventional devices typically default to maximum output (8V at 1.5 ms) for ATP therapy delivery. Given this, even the 7V threshold obtained in the second acute experiment could be satisfactory for ATP therapy.

The ability to capture the heart at low pacing thresholds was dependent upon electrode position. As observed through these experiments, the substernal/retrosternal pacing electrode provide the best outcomes when positioned approximately over the ventricular surface of the cardiac silhouette, which is easily observed via fluoroscopy and encompasses a reasonably large target area for lead placement. In the third acute experiment, for example, capture was achieved at three separate positions, with the lead tip at approximately ribs 4, 5 and 6, all of which were near the ventricular surface of the cardiac silhouette.

Pacing thresholds increased with shorter pulse durations. In many instances, however, low pacing thresholds were obtained even at short pulse widths, especially when the substernal/retrosternal pacing electrode was positioned over the ventricular surface of the cardiac silhouette. In other instances, longer pulse durations (10-20 ms) were necessary to obtain capture or to achieve lower capture thresholds.

Across experiments, it was possible to pace from the substernal/retrosternal lead to an active can emulator positioned near the animal's side (unipolar) and also from the substernal/retrosternal lead to a subcutaneous ICD lead (unipolar). If a subcutaneous ICD system incorporated a pacing lead, placed substernally/retrosternally, for the purpose of anti-tachycardia pacing, both of the aforementioned unipolar pacing configurations would be available for a physician to choose from.

These experiments also demonstrated the ability to pace in a bipolar configuration entirely under the sternum (4194 tip (−) to 4194 ring (+), substernally/retrosternally), indicating that either a bipolar lead positioned under the sternum might be used for anti-tachycardia pacing purposes.

Overall, the results of these acute experiments demonstrate the ability to pace the heart from a substernal/retrosternal location, with the lead not entering the vasculature or the pericardial space, nor making intimate contact with the heart. The low threshold values obtained when pacing from a substernal/retrosternal lead location in these acute experiments suggest that pain-free pacing for the purpose of anti-tachycardia pacing in a subcutaneous ICD system is within reach.

In some instances, electrodes of pacing lead 18 may be shaped, oriented, designed or otherwise configured to reduce extra-cardiac stimulation. FIG. 9 is a schematic diagram illustrating an example electrode configuration for pacing lead 18. In the example of FIG. 9, electrode 100 is attached to the underside of a pad 102. Pad 102 may be constructed of a non-conductive material such as a polymer. Pacing lead 18 may be anchored to under the sternum in such a manner to direct or point electrode 100 toward heart 26. In this manner, pacing pulses delivered by ICD 14 via the pacing lead are directed toward heart 26 and not outward toward skeletal muscle. The electrode illustrated in FIG. 9 may be incorporated within a lead, such as pacing lead 18. In some instances, pad 102 may also provide an anchoring mechanism such as an adhesive. FIG. 9 illustrates one example design of an electrode configured to reduce extra-cardiac stimulation by focusing or directing or pointing the stimulation energy toward heart 26. However, other configurations of electrodes may be utilized to perform such a function. As another example, one or both of electrodes 32 and 34 may be partially coated or masked with a polymer (e.g., polyurethane) or another coating material (e.g., tantalum pentoxide) on one side or in different regions so as to direct the pacing signal toward heart 26 and not outward toward skeletal muscle.

Figure 10A:
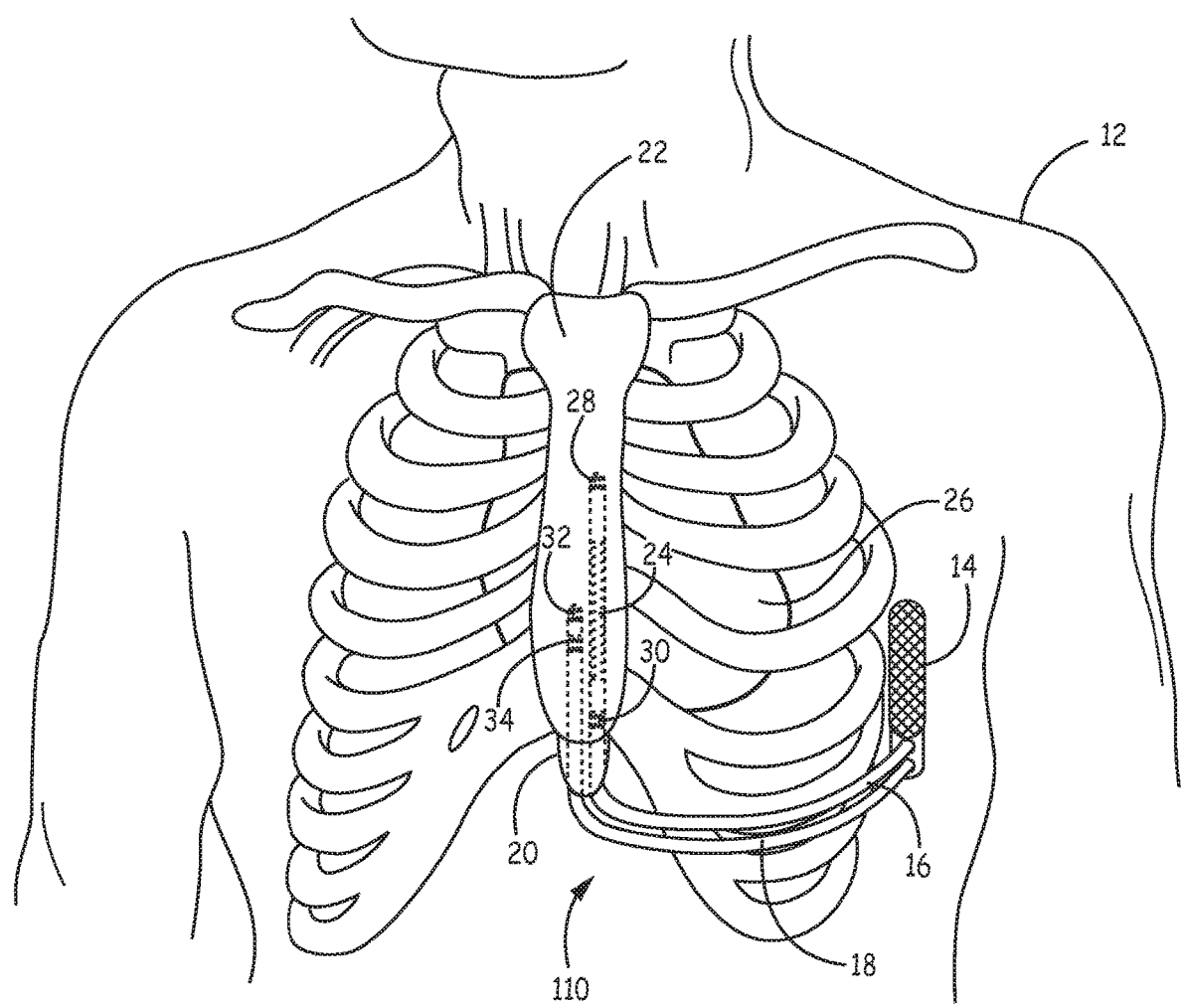
FIG. 10A is a front view of a patient implanted with another example implantable cardiac system having a substernal defibrillation lead and pacing lead.
Figure 10B:
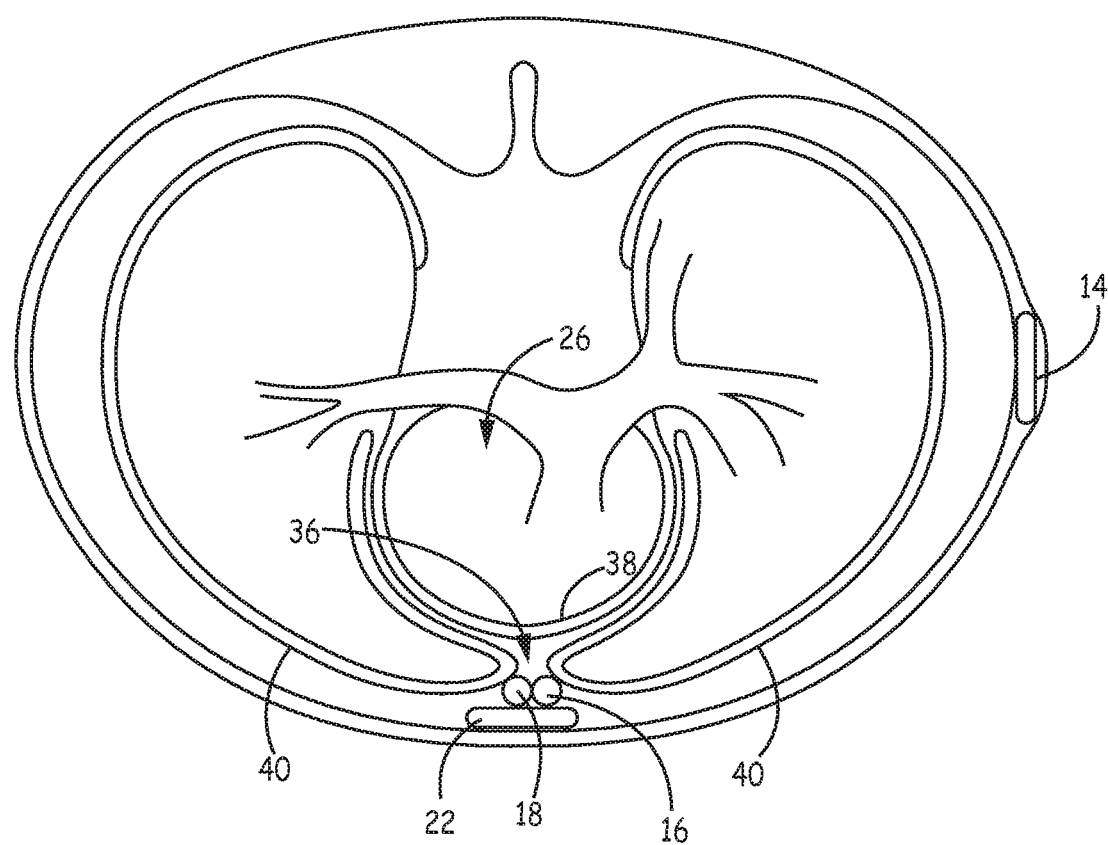
FIG. 10B is a transverse view of the patient with the implantable cardiac system of FIG. 10A.

FIGS. 10A and 10B are conceptual diagrams of patient 12 implanted with another example implantable cardiac system 110. FIG. 10A is a front view of patient 12 implanted with implantable cardiac system 110. FIG. 10B is a transverse view of patient 12 with implantable cardiac system 110.

Implantable cardiac system 110 conforms substantially to implantable cardiac system 10 of FIGS. 1A-1C, but defibrillation lead 16 of system 110 is implanted at least partially in the substernal/retrosternal space. In this manner, both defibrillation lead 16 and pacing lead 18 are implanted within the substernal space. Like pacing lead 18 of FIGS. 1A-1C, defibrillation lead 16 extends subcutaneously from ICD 14 toward xiphoid process 20, and at a location near xiphoid process 20 bends or turns and extends superior in the substernal space. In one example, the distal portion of defibrillation lead 16 may be placed in anterior mediastinum 36 similar to lead 18. In this manner, ICD 14 may be configured to deliver both defibrillation therapy and pacing therapy to patient 12 substernally. In other instances, defibrillation lead 16 and/or pacing lead 18 may be implanted elsewhere in the substernal space.

The benefits of placing pacing lead 18 in this location are described in detail above. Placing defibrillation lead 16 in the substernal space also provides a number of advantages. As described above, ICD 14 generates and delivers defibrillation energy of approximately 80 Joules (J) when defibrillation lead 16 is implanted subcutaneously. Placing defibrillation lead 16 in the substernal space significantly may reduce the amount of energy that needs to be delivered to defibrillate heart 26. As one example, ICD 14 may generate and deliver cardioversion or defibrillation shocks having energies of less than 80 J. As another example, ICD 14 may generate and deliver cardioversion or defibrillation shocks having energies of less than 65 J. As one example, ICD 14 may generate and deliver cardioversion or defibrillation shocks having energies of less than 60 Joules (J). In some instances, ICD 14 may generate and deliver cardioversion or defibrillation shocks having energies between 40-50 J. In other instances ICD 14 may generate and deliver cardioversion or defibrillation shocks having energies between 35-60 J. In still other instances, ICD 14 may generate and deliver cardioversion or defibrillation shocks having energies less than 35 J. As such, placing defibrillation lead 16 within the substernal space, e.g., with the distal portion substantially within anterior mediastinum 36, may result in reduced energy consumption and, in turn, smaller devices and/or devices having increased longevity.

Various examples have been described. These and other examples are within the scope of the following claims.

The invention claimed is:

1. An implantable cardioverter-defibrillator (ICD) system comprising:
    an ICD configured to be implanted subcutaneously in a patient;
    a defibrillation lead having a proximal portion coupled to the ICD and a distal portion having a defibrillation electrode, the ICD being configured to deliver a defibrillation shock to a heart of the patient via the defibrillation electrode; and
    a pacing lead comprising a first elongated body that includes a distal portion having one or more electrodes and a proximal portion coupled to the ICD, the distal portion of the pacing lead having a cylindrical shape along a length of the distal portion to be implanted at least partially along a posterior side of a sternum within an anterior mediastinum of the patient such that the one or more electrodes is physically isolated from a pericardium of the patient, the ICD being configured to deliver pacing pulses to a ventricle of the heart of the patient via at least a first electrode of the one or more electrodes and deliver pacing pulses to an atrium of the heart of the patient via at least a second electrode of the one or more electrodes of the pacing lead, the first electrode being different than the second electrode, with the distal portion of the pacing lead implanted at least partially along the posterior side of the sternum within an anterior mediastinum of the patient such that the one or more electrodes are physically isolated from the pericardium of the patient, wherein the defibrillation lead comprises a second elongated body separate from the first elongated body.

2. The ICD system of claim 1, wherein the ICD is configured to provide at least one of anti-tachycardia pacing (ATP) to the heart of the patient via the one or more electrodes of the pacing lead, bradycardia pacing to the heart of the patient via the one or more electrodes of the pacing lead, and post-shock pacing to the heart of the patient via the one or more electrodes of the pacing lead.

3. The ICD system of claim 1, wherein the ICD is configured to deliver the pacing pulses having pulse widths greater than two (2) milliseconds.

4. The ICD system of claim 1, wherein the ICD is configured to deliver the pacing pulses having pulse widths between two (2) and three (3) milliseconds.

5. The ICD system of claim 1, wherein the ICD is configured to deliver the pacing pulses having pulse widths between approximately one and a half (1.5) milliseconds and twenty (20) milliseconds.

6. The ICD system of claim 1, wherein the ICD is configured to deliver the pacing pulses having pulse widths greater than two (2) milliseconds and less than eight (8) milliseconds.

7. The ICD system of claim 1, wherein the ICD is configured to deliver the pacing pulses having pulse amplitudes between approximately one (1) and twenty (20) volts.

8. The ICD system of claim 1, wherein the ICD is configured to, using the one or more electrodes of the pacing lead, sense electrical signals corresponding to cardiac activity of the heart of the patient and detect one of ventricular tachycardia and ventricular fibrillation based on the sensed signals.

9. The ICD system of claim 1, wherein:
the defibrillation lead includes one or more sensing electrodes to sense electrical signals corresponding to cardiac activity of the heart of the patient;
the one or more electrodes of the pacing lead sense electrical signals corresponding to cardiac activity of the heart of the patient; and
the ICD analyzes the sensed signals from both the defibrillation lead and the pacing lead to detect one of ventricular tachycardia and ventricular fibrillation.

10. The ICD system of claim 1, wherein the ICD is configured to, using the one or more electrodes of the pacing lead, sense electrical signals corresponding to cardiac activity of the heart of the patient and provides the pacing pulses based on the sensed electrical activity of the heart.

11. The ICD system of claim 1, wherein the defibrillation lead includes one or more sensing electrodes to sense, by the ICD, electrical signals corresponding to cardiac activity of the heart of the patient and wherein the ICD is configured to deliver the pacing pulses based on the electrical activity sensed by the of the defibrillation lead.

12. The ICD system of claim 1, wherein the distal portion of the defibrillation lead is configured to be implanted substantially within the anterior mediastinum of the patient.

13. The ICD system of claim 1, wherein the distal portion of the defibrillation lead is configured to be implanted subcutaneously between a skin of the patient and at least one of a sternum or ribs of the patent.

14. The ICD system of claim 1, wherein the one or more electrodes in the distal portion of the pacing lead are ring electrodes.

15. An implantable cardioverter-defibrillator (ICD) system comprising:
an ICD configured to be implanted subcutaneously in a patient;
a first lead having a proximal portion coupled to the ICD and a distal portion having one or more electrodes, wherein the ICD is configured to deliver electrical stimulation therapy to a heart of the patient via the one or more electrodes of the first lead; and
a second lead comprising a first elongated body that includes a proximal portion coupled to the ICD and a distal portion having one or more electrodes, the distal portion of the second lead having a cylindrical shape along a length of the distal portion to be implanted in a substernal space at least partially along a posterior side of a sternum within an anterior mediastinum of the patient such that the at least one electrode is physically isolated from a pericardium of the patient, the ICD being configured to deliver pacing pulses to a ventricle of the heart of the patient via at least a first electrode of the one or more electrodes of the second lead and deliver pacing pulses to an atrium of the heart of the patient via at least a second electrode of the one or more electrodes of the second lead, the first electrode being different than the second electrode,
wherein the ICD is configured to:
obtain electrical signals of the heart of the patient sensed from the substernal space of the patient using the one or more electrodes of the second lead,
detect a tachycardia using the sensed electrical signals, and
deliver electrical stimulation therapy to the patient using the one or more electrodes of the first lead.

16. The system of claim 15, wherein at least one electrode of the one or more electrodes of the first lead comprises a defibrillation electrode and the ICD is configured to deliver defibrillation shocks to the heart of the patient via at least the defibrillation electrode.

17. The system of claim 16, wherein at least one electrode of the one or more electrodes of the first lead comprises a pace/sense electrode and the ICD is configured to deliver pacing pulses to the heart of the patient via at least the pace/sense electrode.

18. The system of claim 17, wherein the pacing pulses comprise at least one of antitachycardia pacing (ATP) or post-shock pacing pulses.

19. The system of claim 17, wherein the ICD is configured to provide antitachycardia pacing (ATP) to the heart of the patient via at least the one or more electrodes of the second lead and to provide post-shock pacing pulses to the heart of the patient via at least the pace/sense electrode of the first lead.

20. An implantable cardioverter-defibrillator (ICD) system comprising:
an ICD configured to be implanted subcutaneously in a patient;
a pacing lead comprising a first elongated body that includes a proximal portion coupled to the ICD and distal portion;
a defibrillation lead having a second elongated body separate from the first elongated body, the second elongated body comprising proximal portion coupled to the ICD and a distal portion;
a first pace/sense electrode, wherein the first pace/sense electrode is located on the distal portion of the first elongated body of the pacing lead;
a second pace/sense electrode, wherein the second pace/sense electrode is located on the distal portion of the second elongated body of the defibrillation lead; and a single defibrillation electrode, wherein the defibrillation electrode is located on the distal portion of the second elongated body of the defibrillation lead;

wherein the distal portion of the first elongated body of the pacing lead is configured to be implanted at least partially along a posterior side of a sternum within an anterior mediastinum of the patient such that the first pace/sense electrode is physically isolated from a pericardium of the patient, wherein the ICD is configured to deliver pacing pulses to a heart of the patient via the first pace/sense electrode and the second pace/sense electrode, and defibrillation shocks to the heart via the defibrillation electrode.

21. The ICD system of claim 20, wherein the ICD is configured to deliver cardiac resynchronization therapy pacing to a plurality of chambers of the heart of the patient via the first pace/sense electrode and the second pace/sense electrode.

* * * * *